(12) United States Patent
Ikonomi et al.

(10) Patent No.: US 7,872,116 B2
(45) Date of Patent: Jan. 18, 2011

(54) IDENTIFICATION OF CELL CULTURE CONTAMINANTS AMONG MOLLICUTES SPECIES BY A PCR BASED ASSAY

(75) Inventors: Pranvera Ikonomi, Springfield, VA (US); Deborah Polayes, Fairfax, VA (US); Karin Cottrill, Sterling, VA (US); Quanyi Li, Cherry Hill, NJ (US)

(73) Assignee: American Type Culture Collection (ATCC), Manassas, VA (US)

( * ) Notice: Subject to any disclaimer, the term of this patent is extended or adjusted under 35 U.S.C. 154(b) by 648 days.

(21) Appl. No.: 11/702,615

(22) Filed: Feb. 6, 2007

(65) Prior Publication Data

US 2008/0187916 A1    Aug. 7, 2008

(51) Int. Cl.
*C07H 21/04* (2006.01)
*C12Q 1/68* (2006.01)
*C12P 19/34* (2006.01)

(52) U.S. Cl. .................. 536/24.33; 435/6; 435/91.2
(58) Field of Classification Search ............. 536/24.33; 435/6, 91.2
See application file for complete search history.

(56) References Cited

U.S. PATENT DOCUMENTS 7,202,027 B1 *   4/2007   Grabowski et al. ............. 435/6

2005/0250112 A1*   11/2005   Padmabandu et al. .......... 435/6

FOREIGN PATENT DOCUMENTS

WO         WO 0123606 A2  *   4/2001

OTHER PUBLICATIONS

Volokhov, D.V. et al. Sequencing of the intergenic 16S-23S rRNA spacer (ITS) region of Mollicutes species and their identification using microarray-based assay and DNA sequencing. Appl. Microbiol. Biotechnol., vol. 71, pp. 680-698, published on line 10, Feb. 2006.*
Lowe et al., A computer program for selection of oligonucleotide primers for polymerase chain reactions. Nucleic Acids Research, vol. 18, No. 7, pp. 1757-1761, 1990.*

* cited by examiner

*Primary Examiner*—Suryaprabha Chunduru
(74) *Attorney, Agent, or Firm*—Bio Intellectual proprty Services LLC (Bio IPS); O. M (Sam) Zaghmout

(57) ABSTRACT

The present invention encompasses nucleic acids, methods, compositions, and kits for sensitive, rapid and specific detection of *Mycoplasma, Acholeplasma, Ureaplasma, Phytoplasma* and *Spiroplasma* species in a sample. The invention utilizes specific primers and amplification methods that permit differentiation between species due to specific amplification of target nucleic acids of contaminating Mollicute cells. In one embodiment, the invention utilizes the differing melting temperatures (Tm) of various potential PCR products to identify whether they are specific target amplification products, non-specific, non-target amplification products, specific positive control products, or primer-dimer products.

12 Claims, 8 Drawing Sheets

Figure 1: Amplification of eight most common *Mycoplasma* species
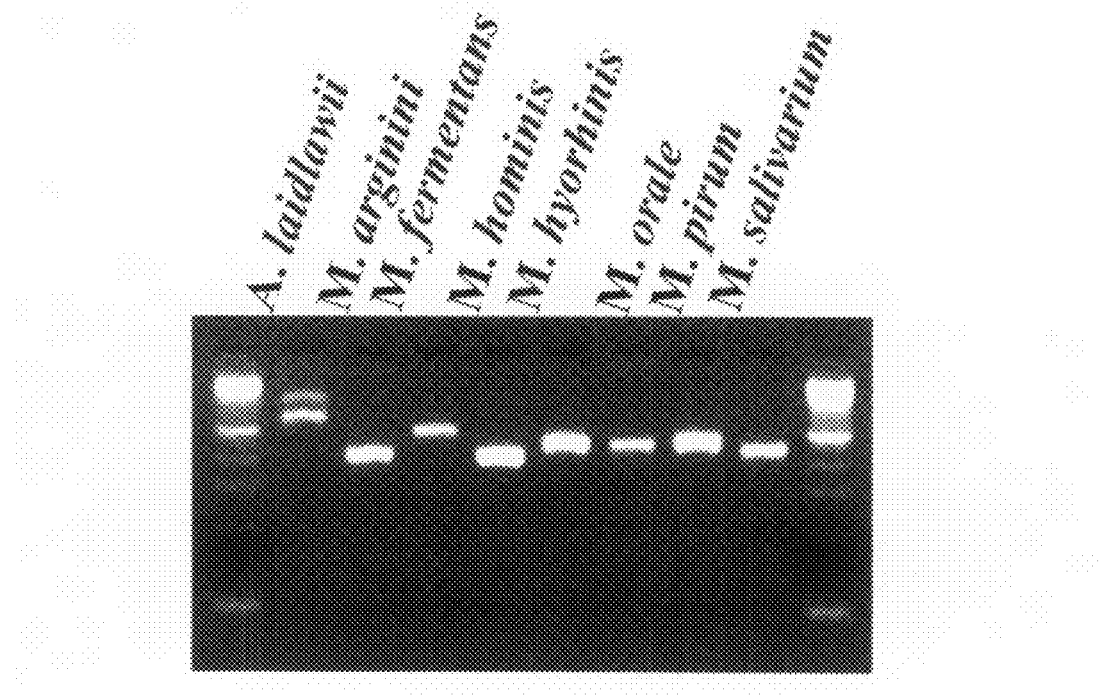

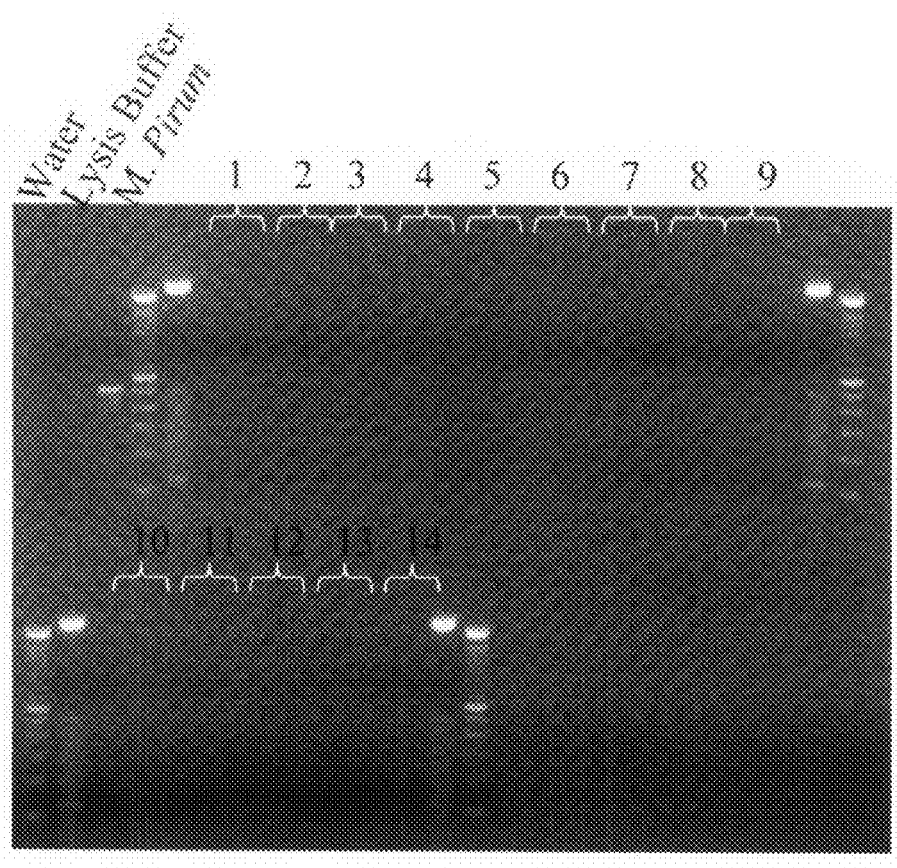
Figure 2: DNA background of host organisms

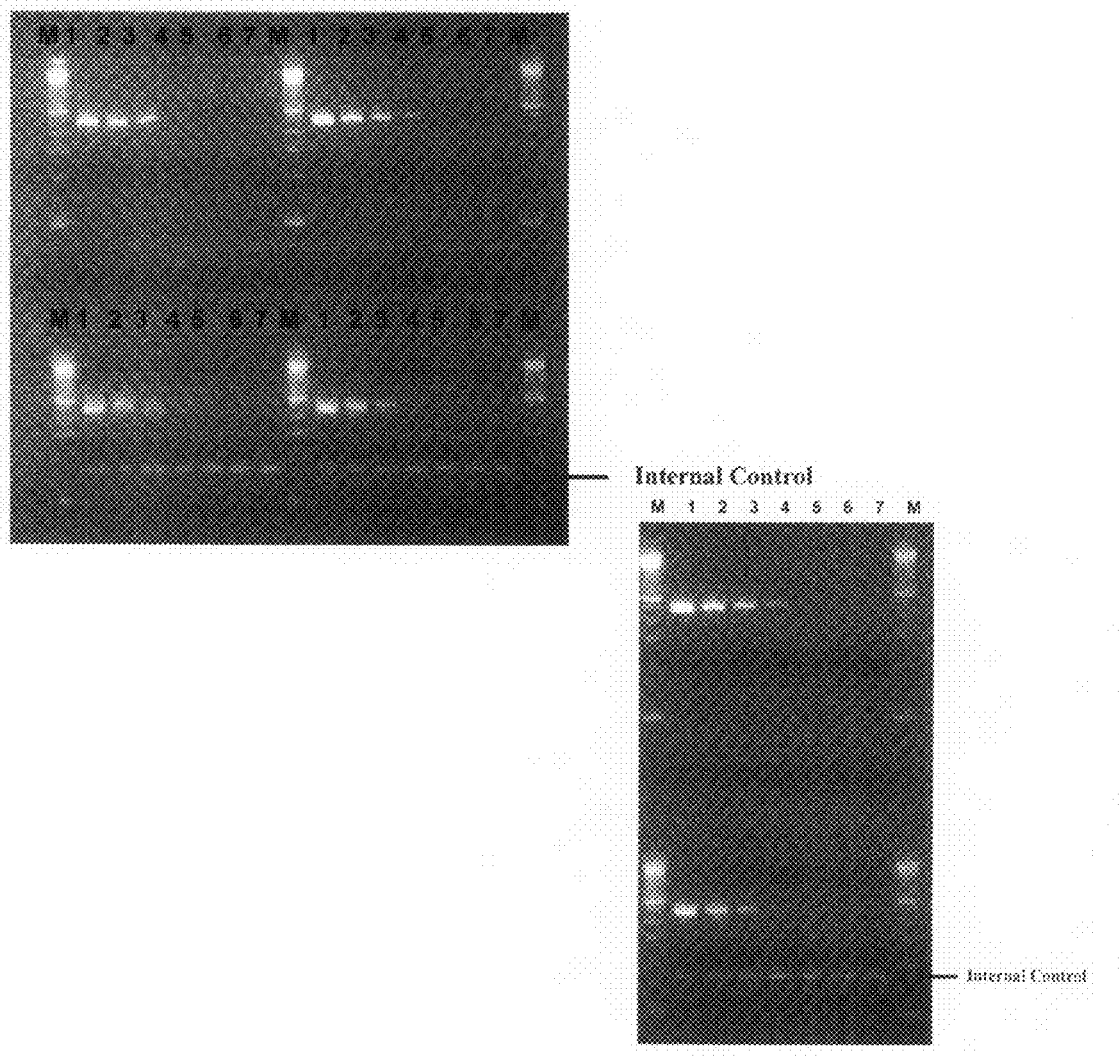

Figure 4: Detection of *E. coli* contamination in the cell culture.
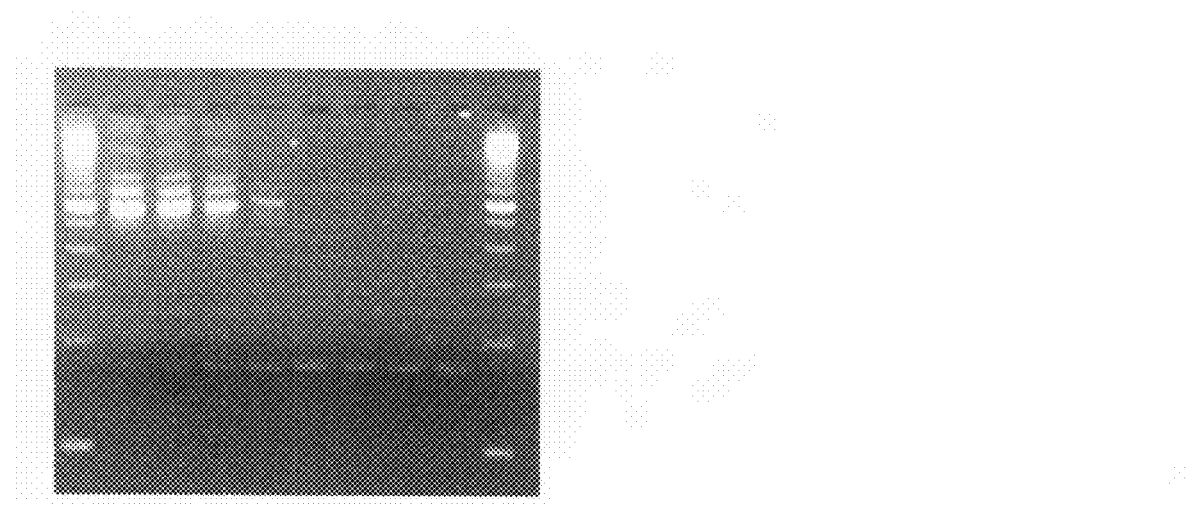

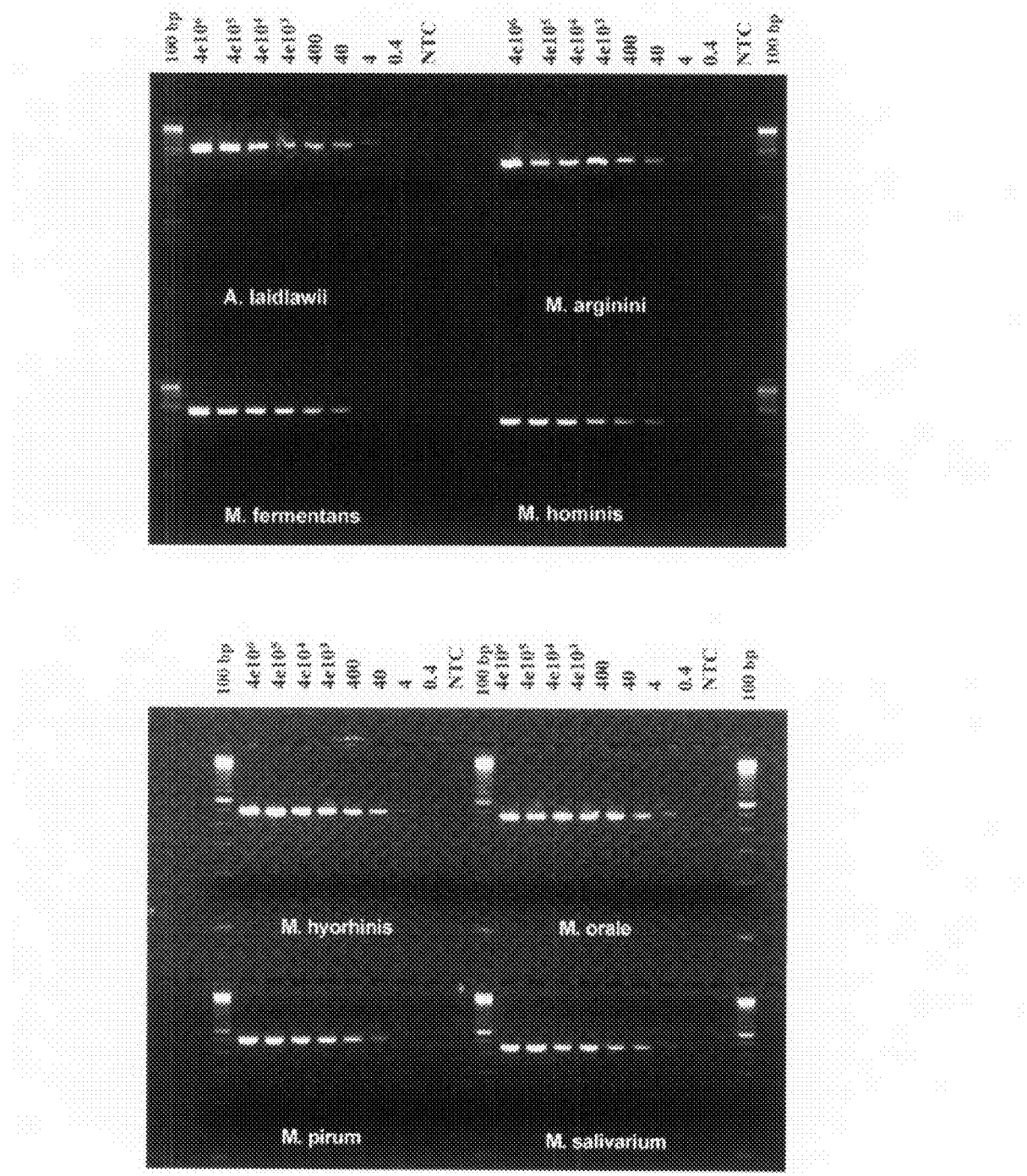
Figure 5: Sensitivity analyses for eight most common *Mycoplasma* species.

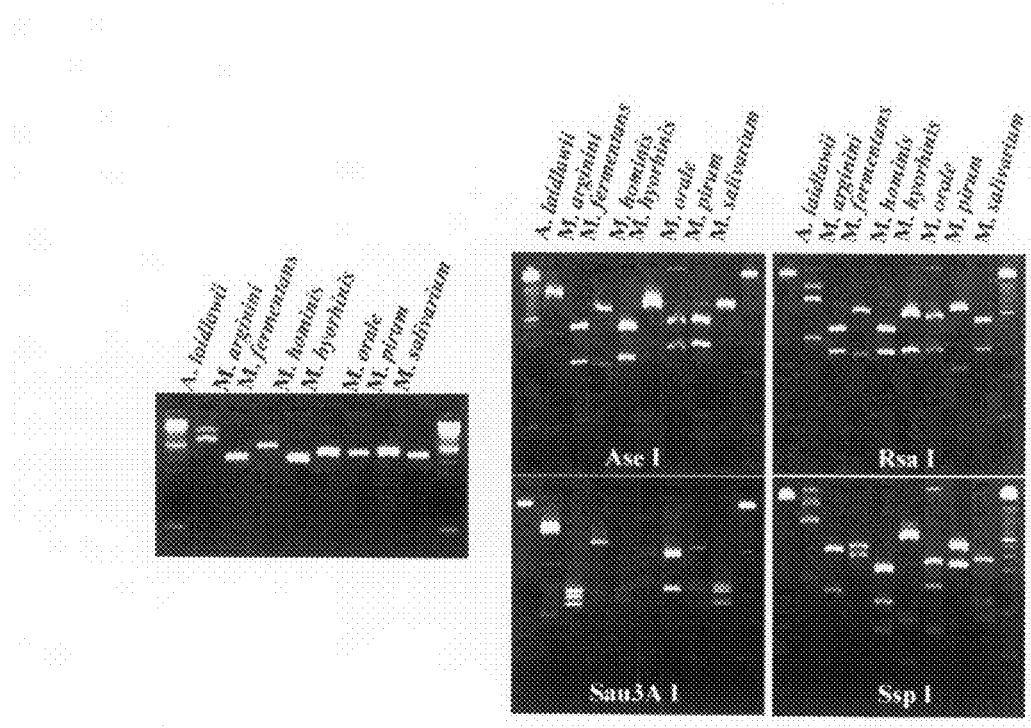
Figure 6: Results of restriction digest analyses for the eight most common types of *Mycoplasma* infections.

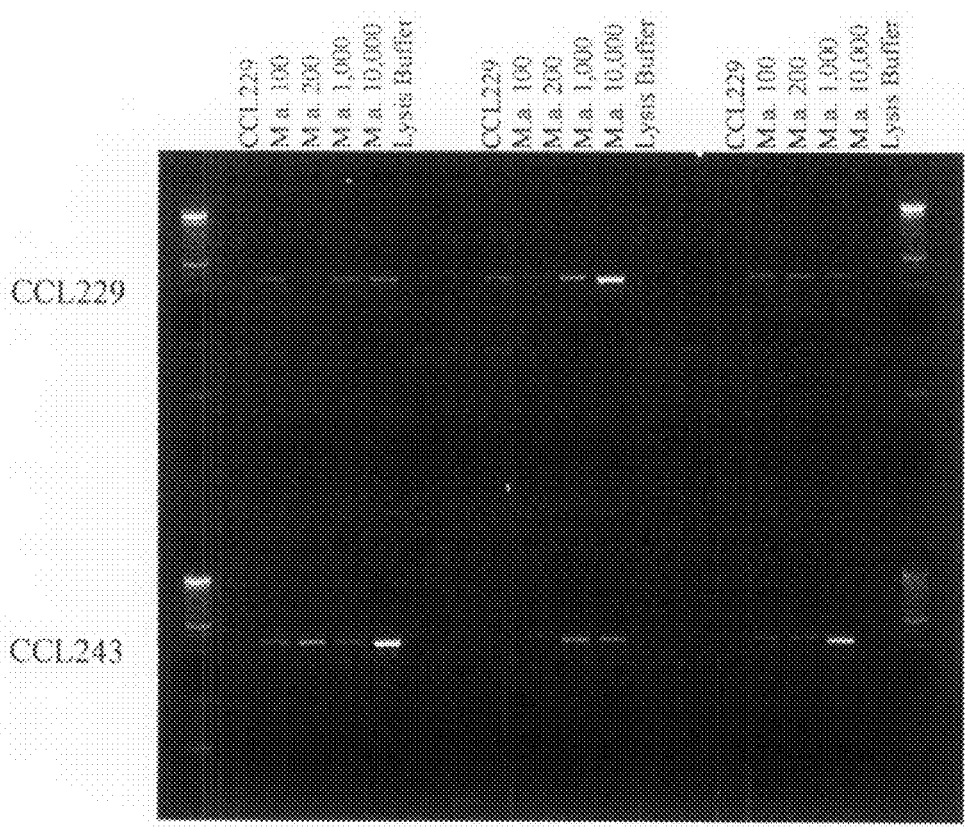
Figure 7: Detection sensitivity assays.

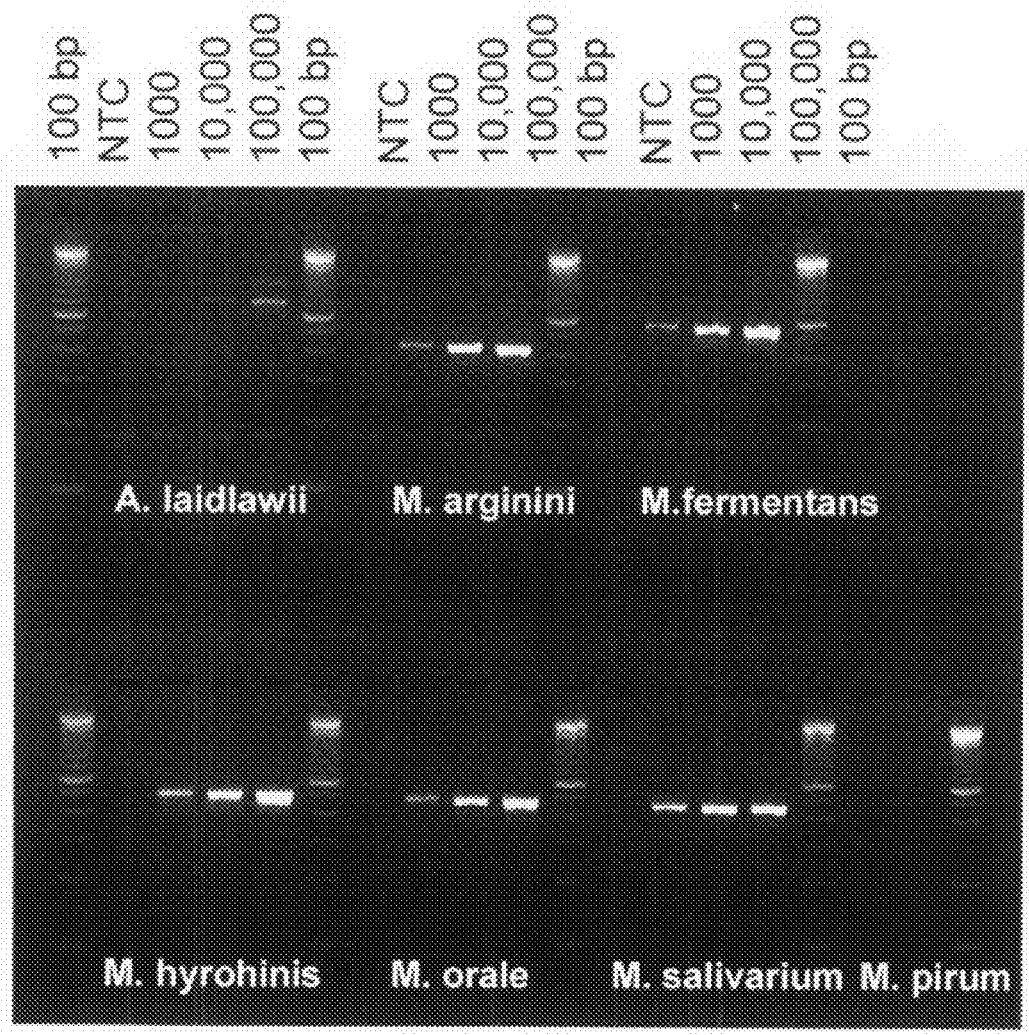
Figure 8: Detection of *Mycoplasma* infection in cell lines.

SEQUENCE LISTING

```
<160> NUMBER OF SEQ ID NOS: 9

<210> SEQ ID NO 1
<211> LENGTH: 22
<212> TYPE: DNA
<213> ORGANISM: Mollicute sp.
<220> FEATURE:
<221> NAME/KEY: primer_bind
<222> LOCATION: (1)..(22)
<223> OTHER INFORMATION: Primers for detection of 49 Mollicute species.
      R is a or g; purine
      Y is c or t/u;pyrimidine

<400> SEQUENCE: 1
gtgaatacgt tctcggrtyt tg                                              22

<210> SEQ ID NO 2
<211> LENGTH: 22
<212> TYPE: DNA
<213> ORGANISM: Mollicute sp.
<220> FEATURE:
<221> NAME/KEY: primer_bind
<222> LOCATION: (1)..(22)
<223> OTHER INFORMATION: Primers for detection of 49 Mollicute species.
      R is a or g; purine
      W is a or t/u

<400> SEQUENCE: 2
atcgcagrtw agcacgtcct tc                                              22
```

```
<210> SEQ ID NO 3
<211> LENGTH: 17
<212> TYPE: DNA
<213> ORGANISM: Mollicute sp.
<220> FEATURE:
<221> NAME/KEY: primer_bind
<222> LOCATION: (1)..(17)
<223> OTHER INFORMATION: Primers for detection of 49 Mollicute species

<400> SEQUENCE: 3
aacgccggtg gcctaac                                                    17

<210> SEQ ID NO 4
<211> LENGTH: 20
<212> TYPE: DNA
<213> ORGANISM: Mollicute sp.
<220> FEATURE:
<221> NAME/KEY: primer_bind
<222> LOCATION: (1)..(20)
<223> OTHER INFORMATION: Primers for detection of 49 Mollicute species

<400> SEQUENCE: 4
cttcaaacgg gattccacgt                                                 20

<210> SEQ ID NO 5
<211> LENGTH: 26
<212> TYPE: DNA
<213> ORGANISM: Mollicute sp.
<220> FEATURE:
<221> NAME/KEY: primer_bind
<222> LOCATION: (1)..(26)
<223> OTHER INFORMATION: Primers for detection of eight most common
      Mollicute species

<400> SEQUENCE: 5
aaggttaagg aacaaagggc acacag                                          26

<210> SEQ ID NO 6
<211> LENGTH: 24
<212> TYPE: DNA
<213> ORGANISM: Mollicute sp.
<220> FEATURE:
<221> NAME/KEY: primer_bind
<222> LOCATION: (1)..(24)
<223> OTHER INFORMATION: Primers for detection of eight most common
      Mollicute species

<400> SEQUENCE: 6
atggtcctcc tatcttcaaa cggg                                            24

<210> SEQ ID NO 7
<211> LENGTH: 27
<212> TYPE: DNA
<213> ORGANISM: Mollicute sp.
<220> FEATURE:
<221> NAME/KEY: primer_bind
<222> LOCATION: (1)..(27)
<223> OTHER INFORMATION: Primers for detection of eight most common
      Mollicute species

<400> SEQUENCE: 7
tcgtaacaag gtatccctac gagaacg                                         27

<210> SEQ ID NO 8
<211> LENGTH: 24
<212> TYPE: DNA
<213> ORGANISM: Mollicute sp.
<220> FEATURE:
```

```
<221> NAME/KEY: primer_bind
<222> LOCATION: (1)..(24)
<223> OTHER INFORMATION: Primers for detection of eight most common
      Mollicute species

<400> SEQUENCE: 8
ttagtattta gccttaccgg gtgg                                          24

<210> SEQ ID NO 9
<211> LENGTH: 25
<212> TYPE: DNA
<213> ORGANISM: Mollicute sp.
<220> FEATURE:
<221> NAME/KEY: primer_bind
<222> LOCATION: (1)..(25)
<223> OTHER INFORMATION: Primers for detection of eight most common
      Mollicute species

<400> SEQUENCE: 9
actagtattt aggcttaccc aatgg                                         25
```

IDENTIFICATION OF CELL CULTURE CONTAMINANTS AMONG MOLLICUTES SPECIES BY A PCR BASED ASSAY

CROSS-REFERENCE TO RELATED APPLICATIONS

FEDERALLY SPONSORED RESEARCH

Not Applicable.

SEQUENCE LISTING OR PROGRAMS

BACKGROUND OF THE INVENTION

Field of the Invention

The information provided below is not admitted to be prior art to the present invention, but is provided solely to assist the understanding of the reader.

The invention relates to the detection of Mollicutes and related species in biological samples. In particular, the invention relates to detection of nucleic acids specific for *Mycoplasma, Acholeplasma, Ureaplasma, Phytoplasma* and *Spiroplasma* species.

The class Mollicutes is one of the smallest known free-living and self replicating forms of life (Razin, S. 1997. Comparative genomics of mycoplasmas. Wien Klin Wochenschr 109:551-6.). Phylogenetic analysis of 16S rRNA gene suggests that Mollicutes originated from Clostridia by regressive evolution as well as genome reduction (Trachtenberg, S. 1998. Mollicutes-wall-less bacteria with internal cytoskeletons. J Struct Biol 124:244-56.). Taxonomically, the lack of cell walls has been used to separate Mollicutes from other bacteria in a class named Mollicutes (Razin, S., D. Yogev, and Y. Naot. 1998. Molecular biology and pathogenicity of mycoplasmas. Microbiol Mol Biol Rev 62:1094-156). The members of this class are summarized as follows:

In the context of the present application, the term "*Mycoplasma*" is intended to embrace all members of the class Mollicutes, not just Mycoplasmatales. In fact, "*Mycoplasma*" is the common term in the art for all of the Mollicutes.

Various species of *Mycoplasma, Acholeplasma, Ureaplasma, Phytoplasma* and *Spiroplasma* are involved in human and animal pathologies. Although the first *Mycoplasma* species was identified in association with bovine pleuropneumonia, it has since been identified as the causative agent of lung disease in humans. Likewise, *Acholeplasma* species have been implicated in waterfowl, swine, cattle, and human disease.

Eight species of *Mycoplasma*, including *Acholeplasma laidlawii, Mycoplasma arginini, M. fermentans, M. hominis, M. hyorhinis, M. orale, M. pirum,* and *M. salivarium* account for greater than 95% of cell culture contamination. The contamination of eukaryotic cell cultures is also a common problem, leading to unreliable experimental results and possibly unsafe biological products.

This represents a serious problem for manufacturers involved in the development and fabrication of biological and pharmaceutical products. In contrast to contamination with other types of bacteria which can be detected in a short period after infection on the basis of visible effects such as cytopathicity, pH change, abnormal growth, or the media appearing turbid, contamination caused by *Mycoplasma* may go undetected without noticeable symptoms (Razin, S. 1997. Comparative genomics of mycoplasmas. Wien Klin Wochenschr 109:551-6. Jung H. Wang S Y, Yang I W, Hsueh D W, Yang W J, Wang T H, Wang: H S. (2003) Detection and treatment of *Mycoplasma* contamination in! cultured cells. Chang Gung Med J. 26: 250-8. Wisher M. (2002) Biosafety and product release testing issues relevant to replication-competent oncolytic viruses, Review. Cancer Gene Ther. 9: 1056-61).

Contamination is typically due to the presence of *Mycoplasma* in the original cell mixture used for culture, cross-contamination of laboratory stocks, contamination from

| Classification | No. Species | Genome Size (kb) | Mol % G + C of genome | Habitat |
| --- | --- | --- | --- | --- |
| Order I: Mycoplasmatales | | | | |
| Family I: *Mycoplasmataceae* | | | | |
| Genus I: *Mycoplasma* | 102 | 580-1,350 | 23-40 | Humans, animals |
| Genus II: *Ureaplasma* | 6 | 760-1,170 | 27-30 | Humans, animals |
| Order II: Entoplasmatales | | | | |
| Family I: *Entoplasmataceae* | | | | |
| Genus I: *Entomoplasma* | 5 | 790-1,140 | 27-29 | Insects, plants |
| Genus II: *Mesoplasma* | 12 | 870-1,100 | 27-30 | Insects, plants |
| Family II: Spiroplasmataceae | | | | |
| Genus I: *Spiroplasma* | 33 | 780-2,220 | 24-31 | Insects, plants |
| Order III: Acholeplasmatales | | | | |
| Family I: *Acholeplasmataceae* | | | | |
| Genus: *Acholeplasma* | 13 | 1,500-1,650 | 26-36 | Animals, some plants, Insects |
| Order IV: Anaeroplasmatales | | | | |
| Family: *Anaeroplasmataceae* | | | | |
| Genus I: *Anaeroplasma* | 4 | 1,500-1,650 | 29-34 | Bovine/ovine rumen |
| Genus II: *Asteroplasma* | 1 | 1,500 | 40 | Bovine/ovine rumen |
| Undefined (1999) | | | | |
| *Phytoplasma* | | 640-1,185 | 23-29 | Insects, plants | compositions added to cell cultures during maintenance or experimental procedures, or transfer from infected laboratory personnel. Although it is widely accepted that ultraviolet and gamma irradiation kills *Mycoplasma*, these small bacteria pass easily through commonly used 0.22-micron sterilization filters. In addition, certain antibiotics are unsuitable for maintaining a *Mycoplasma*-free culture because of the lack of a *Mycoplasma* cell wall. Some studies suggest that the prevalence of *Mycoplasma* contamination in cell cultures is as high as 15% (McGarrity G J and Kotani H. 1985. in The mycoplasmas Vol IV. (Razin S and Barile M F eds) p. 353-390. Academic Press).

Detailed analysis revealed that over 95% of the cases have been linked to infection caused by *M. arginini, M. fermentans, M. hyorhinis, M. orale, M. homonis, M. pirum, M. salivarum*, and *A. laidlawii* (Cobo, F., G. N. Stacey, C. Hunt, C. Cabrera, A. Nieto, R. Montes, J. L. Cortes, P. Catalina, A. Barnie, and A. Concha. 2005. Microbiological control in stem cell banks: approaches to standardisation. Appl Microbiol Biotechnol: 1-11.; Langdon, S. P. 2004. Cell culture contamination: an overview. Methods Mol Med 88:309-17. Razin, S. 1997. Comparative genomics of mycoplasmas. Wien Klin Wochenschr 109:551-6.; Uphoff C C, Drexler H G. (2002) Comparative PCR analysis for s detection of *Mycoplasma* infections in continuous cell lines. In Vitro Cell Dev Anim. 38: 79-85). Such contamination can adversely affect experiments by altering eukaryotic cell surface antigens, chromosomal structure, metabolic rates, protein expression patterns, and transfection efficiency.

A major problem with mycoplasma is that their contamination is often covert, and unlike bacterial detection, cannot be easily visualized. Their resistance to antibiotics and ability to pass through normal bacterial sterilization filters means that they can evade typical precautions of cell culture technique. As a result of the negative impact of having these contaminations going undetected, it has become evident that continuous screening is essential for any cell culture laboratory.

Detection of *Mycoplasma* in cultured cells and tissues is thus critical for the reliability and reproducibility of experimental data. Traditional methods of detection are difficult and time consuming, due to the fastidiousness and slow growth of *Mycoplasma* species in culture (Barile, M. F. & Razin, S. (eds) *The Mycoplasmas* Vol. 1 (Academic, New York, 1979).). *Mycoplasma* culture tests require 15-30 days and the interpretation of the data requires a trained eye and, while staining with 4',6'-diamidino-2-phenylindole hydrochloride (DAPI) or Hoechst stain reduces turn-around time compared to the culture method, the results can still be difficult to interpret. Immunofluorescence detection is also subjective and insensitive, particularly for *Acholeplasma*.

A number of specific *Mycoplasma, Acholeplasma, Ureaplasma, Phytoplasma* and/or *Spiroplasma* detection assays for detection in both clinical and cell culture settings have been described, for example by: Harasawa et al., Res. Microbiol. 144:489-493, 1993; Blazek et al., J. Immunol. Meth. 131:203-212, 1990; Hopert et al., J. Immunol. Meth. 164:91-100, 1993; McGarrity et al., In Vitro Cell. Dev. Biol. 22:301-304, 1986; Uphoff et al., Leukemia 6:335-341, 1992; van Kuppeveld, Appl. Environ. Microbiol. 58:2606-2615, 1992; van Kuppeveld, Appl. Environ. Microbiol. 60:149-152, 1994; Wirth et al., Cytotechnology 16:67-77, 1994; Corless et al., J. Clin. Microbiol. 38:1747-1752, 2000; Kong et al., Appl. Environ. Microbiol. 67:3195-3200, 2001; Yoshida et al., J. Clin. Microbiol. 40:1451-1455, 2002; Loens et al., J. Clin. Microbiol. 40:339-1345, 2002; and Eastick et al., J. Clin. Pathol.: Mol. Pathol. 56:25-28, 2003.

In addition, Uphoff et al., Leukemia 16:289-293, 2002, describes an assay using a mixture of 9 different oligonucleotide primers that amplify 16S rRNA genes from *M. arginini, M. fermentans, M. hominis, M. hyorhinis, M. orale*, and *A. laidlawii*. Further, Dussurget and Roulland-Dussoix, Appl. Environ. Microbiol. 60:953-959, 1994, describes the use of a mixture of polymerase chain reaction (PCR) primers that amplify 16S rRNA gene sequences to detect *M. arginini, A. laidlawii, M. hyorhinis, M. orale*, and *M. fermentans*.

Some kits to detect *Mycoplasma* are commercially available. For example, the *Mycoplasma* Plus™ PCR Primer Set kit (Cat. # 302008, Stratagene, La Jolla, Calif.) uses PCR and restriction fragment analysis to detect the presence, and identify the particular species, of *Mycoplasma* or *Acholeplasma* in a sample. Likewise, the MycoSensor™ PCR Assay Kit (Cat. # 302108, Stratagene, La Jolla, Calif.) is a gel-based PCR assay for the detection of *Mycoplasma* and *Acholeplasma* species. The ATCC *Mycoplasma* detection kit (Cat. # 90-1001K, American Type Culture Collection, Manassas, Va.) used a nested PCR process to amplify the conserved region between 16S and 23S rRNA. In addition, a PCR *Mycoplasma* detection set from Takara Bio Inc. (Otsu, Shiga, Japan) amplifies the conserved region between 16S and 23S rRNA. The MycoTect™ kit (Cat. No. 15672-017, Gibco/Invitrogen, Carlsbad, Calif.) is also available, and detects *Mycoplasma* directly in cell culture using 6-MPDR.

In addition to these kits, a real-time *Mycoplasma* detection kit is commercially available. The VenorGeM-QP® from Minerva Biolabs (Berlin, Germany) targets the 16S rDNA of *Mycoplasma*, and utilizes two probes for detection, each with a different fluorescent dye. According to the manufacturer, the kit can detect as few as 30 copies of a *Mycoplasma* genome. The protocol provided by the manufacturer states that 45 cycles of amplification should be used. However, the manufacturer does not state whether 45 amplification cycles is sufficient to detect as few as 30 copies of a *Mycoplasma* genome.

Furthermore, it is known in the art to use SYBR® Green (Molecular Probes, Eugene, Oreg.) for quantitative PCR (QPCR) applications (e.g., Brilliant® SYBR® Green QPCR and QRT-PCR products from Stratagene (La Jolla, Calif.) under product numbers 600546, 600548, 600552, and others); the DyNAmo™ HS SYBR® Green QPCR kit from Finnzymes (Espoo, Finland); Platinum® SYBR® Green qPCR SuperMix UGD (Invitrogen, Carlsbad, Calif.); SYBR® Green JumpStart Taq ReadyMix (Sigma, St. Louis, Mo.); SYBR® Green QPCR Master Mix (Applied Biosystems, Foster City, Calif.); and the QuantiTect™ SYBR® Green PCR and RT-PCR kit provided by QIAGEN (Valencia, Calif.)). However, none of these products are described as having particular advantages with respect to *Mycoplasma* or *Acholeplasma* detection.

While useful for detection of various nucleic acids and bacteria, some of the methods, kits, and systems discussed above have at least one limitation, which, if overcome, would improve its usefulness.

In the present invention, we describe a sensitive and specific PCR-based assay for detecting contamination by mycoplasma in a cell culture system. This assay provides carefully selected specific primers that are designed for use in a PCR assay which are able to generate an amplicon that can then be digested with restriction enzymes to generate specific and unique fragment(s) for each of the mycoplasma species.

In the present invention, the primers are designed from a nucleic acid sequence in the conserved areas of 16S-23S intergenic region and are carefully selected so that they can detect a high number of mollicute species with a detection sensitivity of 100 copies per sample. The assay involves a single stage PCR. The assay is rapid as well as sensitive. The identity or the genotype of the contaminating Mollicute cells from a number of species can be confirmed further by digesting the PCR-generated amplicons with restriction endonuclease.

SUMMARY OF THE INVENTION

The present invention encompasses nucleic acids, methods, compositions, and kits for sensitive, rapid and specific detection of *Mycoplasma, Acholeplasma, Ureaplasma, Phytoplasma* and *Spiroplasma* species in a sample. The invention utilizes specific primers and amplification methods that permit differentiation between species due to specific amplification of target nucleic acids of contaminating Mollicute cells. In embodiments, the invention utilizes the differing melting temperatures (Tm) of various potential PCR products to identify whether they are specific target amplification products, non-specific, non-target amplification products, specific positive control products, or primer-dimer products.

In a first aspect, the invention provides nucleic acids that can be used in detecting *Mycoplasma* species, *Acholeplasma* species, *Ureaplasma* species, *Phytoplasma* species *Spiroplasma* species, or combinations of one or more species from these five genera. The nucleic acids can be oligonucleotides (oligonucleotide(s), primer(s), oligo(s), fragment(s) are all equivalent and are used interchangeably in the patent specification) that can function as primers for acellular amplification reactions. The nucleic acids can also be genomic or sub-genomic nucleic acids that can be used as controls for monitoring the progression, specificity, and/or sensitivity of the methods of the invention.

In a second aspect, the invention provides methods of acellular amplification of target nucleic acids. The methods of the invention use at least two oligonucleotides to specifically amplify *Mycoplasma, Acholeplasma, Ureaplasma, Phytoplasma* and/or *Spiroplasma* nucleic acids, while essentially avoiding amplification of nucleic acids from other bacteria or eukaryotes. In general, the methods comprise providing purified target nucleic acids, and amplifying and detecting target sequences within the target nucleic acids.

In a third aspect, the invention provides compositions. In general, the compositions comprise at least two oligonucleotide primers that can be used to specifically amplify *Mycoplasma, Acholeplasma, Ureaplasma, Phytoplasma* and/or *Spiroplasma* nucleic acids. The compositions can also contain reagents, solvents, and other nucleic acids for practicing the methods of the invention.

In a fourth aspect, the invention provides kits for detecting *Mycoplasma, Acholeplasma, Ureaplasma, Phytoplasma* and/or *Spiroplasma* species in a sample. The kits can comprise, in one or more packaged combinations, two or more oligonucleotide primers, reagents for performing the methods of the invention, solvents for performing the methods of the invention, and nucleic acid templates for use as positive controls or specificity controls.

BRIEF DESCRIPTION OF THE FIGURES

The foregoing summary, as well as the following detailed description of the invention, will be better understood when read in conjunction with the appended drawings. For the purpose of illustrating the invention, there are shown in the drawings, certain embodiment(s) which are presently preferred. It should be understood, however, that the invention is not limited to the precise arrangements and instrumentalities shown. Drawings are not necessary to scale. Certain features of the invention may be exaggerated in scale or shown in schematic form in the interest of clarity and conciseness.

FIG. 1: Amplification of eight most common *Mycoplasma* species.

FIG. 2: DNA background of host organisms.

Water and Lysis buffer are used as negative controls. 100 bp and 50 bp markers are loaded on each side of the gel. $10^6$ and $10^5$ cells are used for each of the cell lines originated from 14 different organisms. 1: Human, 2: Hamster, 3: Horse, 4: Rat, 5: Mouse, 6: Bovine, 7: Cat, 8: Dog, 9: Rabbit, 10: Goat, 11: Rhesus Monkey; 12: African Green Monkey; 13: Pig, 14: Sheep FIG. 3: Optimization of internal control.

Upper Panel: 1-7 Serial dilutions ($10^5$, $10^4$, $10^3$, $10^2$, $10^1$, 1 and 0 copies) of *M. hyorhinis*.

Lower Panel: 1-7 Serial dilutions ($10^5$, $10^4$, $10^3$, $10^2$, $10^1$, 1 and 0 copies) of *M hyorhinis* in the presence of 3fg (~600 copies) of internal control. M: 50 by DNA marker. Each experiment is performed in duplicate.

FIG. 4: Detection of *E. coli* contamination in the cell culture.

Serial dilutions of $10^8$-$10^2$ cells were used to test for primer specificity. Upper Panel; *E coli* lysates; 1; $10^8$cells, 2: $10^7$cells, 3: $10^6$cells, 4: $10^5$cells, 5: $10^4$cells, 6: $10^3$cells, 7: $10^2$cells; M; 100 bp marker. Lower Panel; *E. coli* lysates; $10^8$cells, 2: $10^7$cells, 3: $10^6$cells, 4: $10^5$cells, 5: $10^4$cells, 6: $10^3$cells, 7: $10^2$cells; 100 copies of the internal control template are added in each reaction prior to PCR.

FIG. 5: Sensitivity analyses for eight most common *Mycoplasma* species.

FIG. 6: Results of restriction digest analyses for the eight most common types of *Mycoplasma* infections.

FIG. 7: Detection sensitivity assays. Known cell concentrations of *Mycoplasma* mixed with $10^5$ eukaryotic cells were lysed and the prepared template was tested for detection of *Mycoplasma* by PCR.

FIG. 8: Detection of *Mycoplasma* infection in cell lines. 100-106 eukaryotic cell lines infected with various *Mycoplasma* species are used for detection of *Mycoplasma*.

DEFINITIONS

Unless defined otherwise, all technical and scientific terms used herein have the same meaning as commonly understood by one of ordinary skill in the art to which this invention belongs. Still, certain elements are defined below for the sake of clarity and ease of reference.

In the context of the present application, the term "*Mycoplasma*" is intended to embrace all members of the class Mollicutes, not just Mycoplasmatales. In fact, "*Mycoplasma*" is the common term in the art for all of the Mollicutes.

By "comprising" is meant including, but not limited to, whatever follows the word "comprising". Thus, use of the term "comprising" indicates that the listed elements are required or mandatory, but that other elements are optional and may or may not be present. By "consisting of" is meant including, and limited to, whatever follows the phrase "consisting of". Thus, the phrase "consisting of" indicates that the listed elements are required or mandatory, and that no other elements may be present. By "consisting essentially of" is meant including any elements listed after the phrase, and limited to other elements that do not interfere with or contribute to the activity or action specified in the disclosure for the listed elements. Thus, the phrase "consisting essentially of" indicates that the listed elements are required or mandatory, but that other elements are optional and may or may not be present depending upon whether or not they affect the activity or action of the listed elements.

As used herein, the phrase "increasing the specificity" of an assay means reducing the frequency or likelihood of false positive assay results. The specificity of an assay is "increased" relative to another assay if there are at least 10% fewer false positive assay results, and preferably at least 20%, 30%, 50%, 75%, 90% or more, up to and including 100% fewer (no false positives) in that assay relative to the other.

As used herein, the term "PCR-based bacterial assay" refers to an assay method for the detection or quantitation of a given bacterial genus or species in a sample, in which the assay comprises PCR amplification with two or more primers that amplify one or more nucleic acid sequences from the targeted bacterial genus or species. A "PCR-based bacterial assay" as the term is used herein is not intended or designed to detect the presence or amount of *E. coli* bacteria in a sample.

As used herein, the term "aligning" when used in reference to nucleic acid sequences means arranging one or more sequences relative one to the other such that the greatest number of identical nucleotides are aligned with each other. BCM Search Launcher (via hypertext transfer protocol at //searchlauncher.bcm.tmc.edu/), formatted with BOX-SHADE 3.2.1 on the Swiss EMBnet node server (available via hypertext transfer protocol on the world wide web at ch.embnet.org/software/BOXform.html) can be used for primer sequence alignments. Multiple sequence alignments can also be performed using the BLAST suite of programs available from the NCBI website (see below).

As used herein, the term "homologous" means evolutionarily related, and can be inferred from nucleic acid identity between two sequences. A host bacterial nucleic acid sequence (e.g., an *E. coli* nucleic acid sequence) is "homologous" to a bacterial target nucleic acid sequence (or vice versa) if it is at least 50% identical to the bacterial target sequence.

In many instances, homology will be well known, for example, the 16S rRNA gene sequences of *Mycoplasma* sp. are well known to be homologous to the 16S rRNA gene sequence from *E. coli* (e.g., the *M. orale* 16S rRNA gene sequence is a known homolog and is 81% identical to the *E. coli* 16S rRNA gene sequence).

In its broadest sense, the term "substantially similar", when used herein with respect to a nucleotide sequence, means a nucleotide sequence corresponding to a reference nucleotide sequence, wherein the corresponding sequence encodes a polypeptide having substantially the same structure and function as the polypeptide encoded by the reference nucleotide sequence, e.g. where only changes in amino acids not affecting the polypeptide function occur. Desirably the substantially similar nucleotide sequence encodes the polypeptide encoded by the reference nucleotide sequence. The percentage of identity between the substantially similar nucleotide sequence and the reference nucleotide sequence (number of complementary bases in the complementary sequence divided by total number of bases in the complementary sequence) desirably is at least 80%, more desirably 85%, preferably at least 90%, more preferably at least 95%, most preferably at least 99%.

The terms "identical" or "percent identity" in the context of two or more nucleic acid or protein sequences, refer to two or more sequences or subsequences that are the same or have a specified percentage of amino acid residues or nucleotides that are the same, when compared and aligned for maximum correspondence, as measured using one of the following sequence comparison algorithms or by visual inspection.

"Substantially identical," in the context of two nucleic acid or protein sequences, refers to two or more sequences or subsequences that have at least 60%, preferably 80%, more preferably 90-95%, and most preferably at least 99% nucleotide or amino acid residue identity, when compared and aligned for maximum correspondence, as measured using one of the following sequence comparison algorithms or by visual inspection. Preferably, the substantial identity exists over a region of the sequences that is at least about 50 residues in length, more preferably over a region of at least about 100 residues, and most preferably the sequences are substantially identical over at least about 150 residues. In a most preferred embodiment, the sequences are substantially identical over the entire length of the coding regions. Furthermore, substantially identical nucleic acid or protein sequences perform substantially the same function.

For sequence comparison, typically one sequence acts as a reference sequence to which test sequences are compared. When using a sequence comparison algorithm, test and reference sequences are input into a computer, subsequence coordinates are designated if necessary, and sequence algorithm program parameters are designated. The sequence comparison algorithm then calculates the percent sequence identity for the test sequence(s) relative to the reference sequence, based on the designated program parameters.

As used herein, the term "hybridizes," when used in reference to an oligonucleotide primer, refers to the formation of a hydrogen-bonded base paired duplex with a nucleic acid having a sequence sufficiently complementary to that of the oligonucleotide primer to permit the formation of such a duplex under the conditions used. As the term is used herein, exact complementarity between an oligonucleotide primer and a nucleic acid sequence is not required, with mismatches permitted as long as the resulting duplex is a substrate for extension by a template-dependent nucleic acid extending enzyme. A nucleic acid sequence is "sufficiently complementary" to an oligonucleotide primer if the primer can form a duplex with a molecule comprising the nucleic acid sequence at 55° C. that can be extended by at least one nucleotide by a template-dependent nucleic acid extending enzyme, e.g., a polymerase, in a solution comprising 10 mM Tris-HCl, pH 8.8, 50 mM KCl, 2.0 mM $MgCl_2$, and 200 µM each of dATP, dCTP, dGTP, and dTTP.

As used herein, the phrase "standard conditions," when used in reference to nucleic acid hybridization, refers to incubation at 55° C. in a buffer containing 15 mM Tris-HCl, pH 8.0, 50 mM KCl, and 2.5 mM $MgCl_2$, or its equivalent. Oligonucleotide primer molecules hybridized to a template nucleic acid (e.g., a *Mycoplasma* 16S rRNA gene or an internal amplification control template) under these conditions will be extended by at least one nucleotide by a template-dependent nucleic acid extending enzyme provided that the 3'-terminal two nucleotides of the primer are base paired to the template.

"Stringent hybridization conditions" and "stringent hybridization wash conditions" in the context of nucleic acid hybridization experiments such as Southern and Northern hybridizations are sequence dependent, and are different under different environmental parameters. Longer sequences hybridize specifically at higher temperatures. An extensive guide to the hybridization of nucleic acids is found in Tijssen (1993) Laboratory Techniques in Biochemistry and Molecular Biology-Hybridization with Nucleic Acid Probes part I chapter 2 "Overview of principles of hybridization and the strategy of nucleic acid probe assays" Elsevier, N.Y., which is hereby incorporated by reference. Generally, highly stringent hybridization and wash conditions are selected to be about 5°

C. lower than the thermal melting point (Tm) for the specific sequence at a defined ionic strength and pH. Typically, under "stringent conditions" a probe will hybridize to its target subsequence, but to no other sequences.

The $T_m$ is the temperature (under defined ionic strength and pH) at which 50% of the target sequence hybridizes to a perfectly matched probe. Very stringent conditions are selected to be equal to the Tm for a particular probe. An example of stringent hybridization conditions for hybridization of complementary nucleic acids which have more than 100 complementary residues on a filter in a Southern or northern blot is 50% formamide with 1 mg of heparin at 42° C., with the hybridization being carried out overnight. An example of highly stringent wash conditions is 0.15M NaCl at 72° C. for about 15 minutes. An example of stringent wash conditions is a 0.2.times.SSC wash at 65° C. for 15 minutes (see, Sambrook, infra, for a description of SSC buffer). Often, a high stringency wash is preceded by a low stringency wash to remove background probe signal. An example of medium stringency wash for a duplex of, e.g., more than 100 nucleotides, is 1.times.SSC at 45° C. for 15 minutes. An example low stringency wash for a duplex of, e.g., more than 100 nucleotides, is 4-6.times.SSC at 40° C. for 15 minutes. For short probes (e.g., about 10 to 50 nucleotides), stringent conditions typically involve salt concentrations of less than about 1.0M Na ion, typically about 0.01 to 1.0 M Na ion concentration (or other salts) at pH 7.0 to 8.3, and the temperature is typically at least about 30° C. Stringent conditions can also be achieved with the addition of destabilizing agents such as formamide. In general, a signal to noise ratio of 2.times. (or higher) than that observed for an unrelated probe in the particular hybridization assay indicates detection of a specific hybridization. Nucleic acids that do not hybridize to each other under stringent conditions are still substantially identical if the proteins that they encode are substantially identical. This occurs, e.g., when a copy of a nucleic acid is created using the maximum codon degeneracy permitted by the genetic code.

The following are examples of sets of hybridization/wash conditions that may be used to clone homologous nucleotide sequences that are substantially identical to reference nucleotide sequences of the present invention: a reference nucleotide sequence preferably hybridizes to the reference nucleotide sequence in 7% sodium dodecyl sulfate (SDS), 0.5 M NaPO.sub.4, 1 mM EDTA at 50° C. with washing in 2.times.SSC, 0.1% SDS at 50° C., more desirably in 7% sodium dodecyl sulfate (SDS), 0.5 M NaPO.sub.4, 1 mM EDTA at 50° C. with washing in 0.1.times.SSC, 0.1% SDS at 50° C., more desirably still in 7% sodium dodecyl sulfate (SDS), 0.5 M NaPO.sub.4, 1 mM EDTA at 50° C. with washing in 0.5.times.SSC, 0.1% SDS at 50° C. preferably in 7% sodium dodecyl sulfate (SDS), 0.5 M NaPO.sub.4, 1 mM EDTA at 50° C. with washing in 0.1.times.SSC, 0.1% SDS at 50° C. more preferably in 7% sodium dodecyl sulfate (SDS), 0.5 M NaPO.sub.4, 1 mM EDTA at 50° C. with washing in 0.1.times.SSC, 0.1% SDS at 65° C.

A further indication that two nucleic acid sequences or proteins are substantially identical is that the protein encoded by the first nucleic acid is immunologically cross reactive with, or specifically binds to, the protein encoded by the second nucleic acid. Thus, the first protein is typically substantially identical to a second protein, for example, where the two proteins differ only by conservative substitutions.

Various biochemical and molecular biology methods are well known in the art. For example, methods of isolation and purification of nucleic acids are described in detail in WO 97/10365, WO 97/27317, Chapter 3 of Laboratory Techniques in Biochemistry and Molecular Biology: Hybridization With Nucleic Acid Probes, Part I. Theory and Nucleic Acid Preparation, (P. Tijssen, ed.) Elsevier, N.Y. (1993); Chapter 3 of Laboratory Techniques in Biochemistry and Molecular Biology: Hybridization With Nucleic Acid Probes, Part 1. Theory and Nucleic Acid Preparation, (P. Tijssen, ed.) Elsevier, N.Y. (1993); and Sambrook et al., Molecular Cloning: A Laboratory Manual, Cold Spring Harbor Press, N.Y., (1989); and Current Protocols in Molecular Biology, (Ausubel, F. M. et al., eds.) John Wiley & Sons, Inc., New York (1987-1999), including supplements such as supplement 46 (April 1999), all of which are incorporated by reference herein.

"Conservatively modified variations" of a particular nucleic acid sequence refers to those nucleic acid sequences that encode identical or essentially identical amino acid sequences, or where the nucleic acid sequence does not encode an amino acid sequence, to essentially identical sequences. Because of the degeneracy of the genetic code, a large number of functionally identical nucleic acids encode any given polypeptide. For instance the codons CGT, CGC, CGA, CGG, AGA, and AGG all encode the amino acid arginine. Thus, at every position where an arginine is specified by a codon, the codon can be altered to any of the corresponding codons described without altering the encoded protein. Such nucleic acid variations are "silent variations" which are one species of "conservatively modified variations." Every nucleic acid sequence described herein which encodes a protein also describes every possible silent variation, except where otherwise noted. One of skill will recognize that each codon in a nucleic acid (except ATG, which is ordinarily the only codon for methionine) can be modified to yield a functionally identical molecule by standard techniques. Accordingly, each "silent variation" of a nucleic acid which encodes a protein is implicit in each described sequence.

Furthermore, one of skill will recognize that individual substitutions deletions or additions that alter, add or delete a single amino acid or a small percentage of amino acids (typically less than 5%, more typically less than 1%) in an encoded sequence are "conservatively modified variations," where the alterations result in the substitution of an amino acid with a chemically similar amino acid. Conservative substitution tables providing functionally similar amino acids are well known in the art. The following five groups each contain amino acids that are conservative substitutions for one another: Aliphatic: Glycine (G), Alanine (A), Valine (V), Leucine (L), Isoleucine (I); Aromatic: Phenylalanine (F), Tyrosine (Y), Tryptophan (W); Sulfur-containing: Methionine (M), Cysteine (C); Basic: Arginine (R), Lysine (K), Histidine (H); Acidic: Aspartic acid (D), Glutamic acid (E), Asparagine (N), Glutamine (Q). See also, Creighton (1984) Proteins, W. H. Freeman and Company. In addition, individual substitutions, deletions or additions which alter, add or delete a single amino acid or a small percentage of amino acids in an encoded sequence are also "conservatively modified variations."

Unless otherwise specifically stated otherwise, as used herein, the terms "*Mycoplasma,*" "*Mycoplasma* species," "*Acholeplasma,*" "*Acholeplasma* species," "*Ureaplasma,*" "*Ureaplasma* species," "*Phytoplasma,*" "*Phytoplasma* species," "*Spiroplasma,*" "*Spiroplasma* species," and *Mycoplasma/Acholeplasma/Ureaplasma/Phytoplasma/Spiroplasma*" are intended to include and encompass all members of the genus *Mycoplasma*, the genus *Acholeplasma*, the genus *Ureaplasma*, the genus *Phytoplasma* and genus *Spiroplasma*.

The terms are used interchangeably, and use of one or another term is not intended to exclude the others, unless specifically stated.

As used herein, the phrase "cross-hybridizes" refers to the hybridization of an oligonucleotide primer designed to hybridize with a *Mycoplasma* species 16S rRNA gene sequence with a 16S rRNA from a non-*Mycoplasma* species.

As used herein, the phrase "does not base pair with" or "is mismatched" means that a given sequence of nucleotides on an oligonucleotide primer does not form complementary hydrogen bonds with an adjacent nucleotide sequence on a nucleic acid molecule. As the phrase is used herein, when one or more 3'-terminal nucleotides on an oligonucleotide primer "do not base pair" with a template nucleic acid molecule, a template-dependent nucleic acid extending enzyme will not extend the primer by one nucleotide or more under annealing and polymerization conditions as follows: 10 µCi of each of $^{33}$P-labeled dATP, dCTP, dGTP, and dTTP (>1000 Ci/mMole), 1×Taq polymerase buffer (10 mM Tris-HCl, pH 8.8, 50 mM KCl, 1.5 mM MgCl$_2$, 0.001% (w/v) gelatin; or its equivalent), 100 nM of primer, 2.0 mM MgCl$_2$, 100 fmol template and 0.04 U/µl of Taq200™ polymerase (Stratagene #600197-51); the mixture is heated at 94° C. for 30 seconds, annealing is performed at 55° C. for 30 seconds, and polymerization is performed at 72° C. for one minute. The presence of one or more labeled species detected by autoradiography when the reaction products are separated on polyacrylamide gel demonstrates the extension of the primer. If there are no labeled species, the terminal nucleotide(s) of the primer "does not base pair with" the template. Alternatively, when the sequence of a potential contaminating template, e.g., an *E. coli* 16S rRNA gene sequence, is known, one can manually or via computer (e.g., using BLAST, with default parameters) align a given primer sequence with the contaminating template sequence. If one or more (e.g., one, two, three) of the 3'-terminal three nucleotides of the primer are not complementary to the template, they "do not base pair" with the template.

As used herein, the phrase "amplification control template" refers to a double- or single-stranded nucleic acid molecule that is added to a nucleic acid amplification reaction to serve as a control for the activity of the template-dependent nucleic acid extending enzyme used in such reaction. Various suitable control templates are known in the art. Amplification of the amplification control template can be distinguished from amplification of the target template by melting temperature or product length.

As used herein, the phrase "template-dependent nucleic acid extending enzyme" refers to an enzyme that catalyzes the template-dependent addition of nucleotides to the 3' end of a nucleic acid strand hybridized to a substantially complementary template nucleic acid strand. A template-dependent nucleic acid extending enzyme useful in the methods disclosed herein will not extend an oligonucleotide primer in which one or more 3'-terminal nucleotides (e.g., the last 3'-terminal nucleotide, the last two 3'-terminal nucleotides, etc.) is not base paired with the template nucleic acid. That is, a template-dependent nucleic acid extending enzyme useful in the methods disclosed herein requires that at least the 3' terminal two nucleotides of the primer strand be base paired with the template. Base pairing of the 3'-terminal two nucleotides of a primer with the template can be determined by alignment of the sequences, either manually or by computer. If the last one or two 3' nucleotides of the primer are complementary to the template, the template-dependent nucleic acid extending enzyme useful in the methods described herein will extend the primer by at least one nucleotide, and preferably more, under conditions as described in the definition of "does not base pair," above. If, on the other hand, the alignment shows that the last one or two nucleotides are not complementary to the template, a template-dependent nucleic acid extending enzyme useful in the methods described herein will not extend the primer by one or more nucleotides under the same conditions.

As used herein, the term "isolated" refers to a population of molecules, e.g., polypeptides, polynucleotides, or oligonucleotides, the composition of which is less than 50% (by weight), preferably less than 40% and most preferably 2%, 1%, 0.5%, 0.2%, 0.1%, or less, contaminating molecules of an unlike nature.

As used herein, the term "set" refers to a group of at least two. Thus, a "set" of oligonucleotide primers comprises at least two oligonucleotide primers.

As used herein, an "oligonucleotide primer" and a "primer" are used interchangeably in their most general sense to include any length of nucleotides which, when used for amplification purposes, can provide a free 3' hydroxyl group for the initiation of DNA synthesis by a DNA polymerase, either using a RNA or a DNA template. DNA synthesis results in the extension of the primer to produce a primer extension product complementary to the nucleic acid strand to which the primer has hybridized. Generally, the primer comprises from 3 to 100 nucleotides, preferably from 5 to 50 nucleotides and even more preferably from 10 to 35 nucleotides. Primers are often selected to be any number of nucleotides between 10 and 25 nucleotides or more in length. The primers of the present invention may be synthetically produced by, for example, the stepwise addition of nucleotides or may be fragments, parts, portions or extension products of other nucleotide acid molecules. The term primer is used generally to encompass both strands of a given sequence (i.e., a given sequence and its complementary sequence).

The probe may have a sense, antisense or complementary sequence of SEQ ID Nos. disclosed in this specification as long as it can hybridize with one of the strands in a double stranded target DNA. The oligonucleotide may be ribonucleotide (RNA), deoxynucleotide (DNA), peptide nucleic acid (PNA) or locked nucleic acid (LNA), and contain modified nucleotides such as Inosine only if it does not change their hybridization characteristics. Preferably, the species-specific or the strain-specific oligonucleotides for detecting *Mycoplasma, Acholeplasma, Ureaplasma, Phytoplasma* and/or *Spiroplasma* may have a base sequence of SEQ ID Nos. Preferably, the genus-specific and species-specific oligonucleotides for detecting *Mycoplasma, Acholeplasma, Ureaplasma, Phytoplasma* and/or *Spiroplasma* may have a base sequence of SEQ ID Nos. of sequences that are listed in this patent application.

"Complementary" refers to the broad concept of sequence complementarity between regions of two polynucleotide strands or between two nucleotides through base-pairing. It is known that an adenine nucleotide is capable of forming specific hydrogen bonds ("base pairing") with thymine or uracil. Similarly, it is known that a cytosine nucleotide is capable of base pairing with a guanine nucleotide. This hydrogen bonding is the basis of the hybridization mentioned in this document.

As used herein, the phrase "extension product" refers to the nucleic acid product of an extension reaction catalyzed by a template-dependent nucleic acid extending enzyme. An "extension product" has been extended by at least one nucleotide by a template-dependent nucleic acid extending enzyme.

As used herein, the phrase "detectably different in size or sequence" means that the extension or amplification product formed by enzymatic extension or amplification of an internal amplification control template can be distinguished from the extension or amplification product of a target nucleic acid on the basis of a difference in size or sequence using techniques known to those of skill in the art or described herein. Conditions are well known for the separation of nucleic acids differing by as little as one nucleotide in length. Thus, the phrase "detectably different in size or sequence" can mean that a molecule differs by at least one nucleotide in length from another. It is preferred, however, that molecules of "detectably different" size differ by more than one nucleotide, e.g., by at least 10 nucleotides, 50 nucleotides, 100 nucleotides, or more. Alternatively, molecules of different sequence can be distinguished, e.g., on the basis of an enzymatic cleavage site or a binding site for a ligand that is present on one nucleic acid molecule but not on the other. Likewise, they can be distinguished based on their respective melting temperatures. Thus, in the context of single stage PCR reactions, this technique can be easier to perform, generate less waste, and provide results faster than other techniques for detecting different sizes or sequences. Such molecules are thus of "detectably different" sequence.

As used herein, the term "silica gel" refers to such gels known in the art (e.g., as described in U.S. Pat. No. 4,923,978, the entirety of which is hereby incorporated by reference), which can be used to separate nucleic acids from other cellular components (e.g., proteins). One non-limiting example of a silica gel according to the invention includes the hydroxylated silica particles provided by Stratagene Inc. (La Jolla, Calif., Cat # 400714).

Unless otherwise defined in the present text, other terms and phrases are used in accordance with their art-recognized meanings.

DETAILED DESCRIPTION OF CERTAIN EMBODIMENTS

Before the subject invention is described further, it is to be understood that the invention is not limited to the particular embodiments of the invention described below, as variations of the particular embodiments may be made and still fall within the scope of the appended claims. It is also to be understood that the terminology employed is for the purpose of describing particular embodiments, and is not intended to be limiting. Instead, the scope of the present invention will be established by the appended claims.

In this specification and the appended claims, the singular forms "a," "an" and "the" include plural reference unless the context clearly dictates otherwise. Unless defined otherwise, all technical and scientific terms used herein have the same meaning as commonly understood to one of ordinary skill in the art to which this invention belongs.

Where a range of values is provided, it is understood that each intervening value, to the tenth of the unit of the lower limit unless the context clearly dictates otherwise, between the upper and lower limit of that range, and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood to one of ordinary skill in the art to which this invention belongs. Although any methods, devices and materials similar or equivalent to those described herein can be used in the practice or testing of the invention, the preferred methods, devices and materials are now described.

All publications mentioned herein are incorporated herein by reference for the purpose of describing and disclosing the subject components of the invention that are described in the publications, which components might be used in connection with the presently described invention.

The information provided below is not admitted to be prior art to the present invention, but is provided solely to assist the understanding of the reader.

The details of one or more embodiments of the invention are set forth in the accompanying drawings and the description below. Other features, objects, and advantages of the invention will be apparent from the description and drawings, and from the claims.

The present invention relates to assay methods and materials for detecting and identifying members of the Mollicutes family, that contaminate a test sample, such as a sample from a cell culture.

*Mycoplasma, Acholeplasma, Ureaplasma, Phytoplasma* and *Spiroplasma* account for a great percentage of cell culture contamination. The assays described herein detect the presence of many of these species in a single assay. Further features of the assays disclosed herein include: 1) consistent amplification of genomic DNA (gDNA) from target *Mycoplasma* species, with as little as 10-100 copies of gDNA per PCR reaction; 2) the reagents and methods described permit, where desired, the production of a PCR product of different sizes for all species of interest; 3) reduction or elimination of false positive assay results caused by the presence of *E. coli* nucleic acid in preparations of recombinant enzymes used to amplify target gene sequences; 4) prevention of carry-over contamination from previous assays; and 5) a robust, well characterized internal amplification control template to control for the presence of inhibitors of the amplification reaction.

In a first aspect, the invention provides nucleic acids that can be used in detecting *Mycoplasma* species, *Acholeplasma* species, *Ureaplasma* species, *Phytoplasma* species, *Spiroplasma* species or combinations of one or more species from these five genera. The nucleic acids can be oligonucleotides that can function as primers for PCR reactions. The nucleic acids can also be primers or genomic or sub-genomic nucleic acids that can be used as controls for monitoring the progression, specificity, and/or sensitivity of the methods of the invention.

Primers according to the invention can specifically hybridize to a *Mycoplasma/Acholeplasma* nucleic acid and permit template-dependent extension of the *Mycoplasma/Acholeplasma* nucleic acid during acellular amplification of the nucleic acid. Suitable primers can be designed by those of skill in the art based on known nucleic acid sequences of *Mycoplasma/Acholeplasma* species. Suitable primers can show perfect identity to the selected, known sequences, or can have less than 100% identity, as long as the identity is sufficient for the primer to specifically hybridize to the *Mycoplasma/Acholeplasma* target nucleic acid and permit extension of the primer under the appropriate conditions. Non-limiting examples of primers suitable for amplifying and detecting various *Mycoplasma/Acholeplasma* species are listed.

PCR-based bacterial detection assays rely upon the ability of a set of primers specific for a given gene or nucleic acid sequence (or set of such sequences sharing common primer hybridization sequences) to direct the amplification of a target bacterial sequence from among a background of non-target sequences. Target bacterial genes are often selected to vary as widely as possible from other known sequences in order to ensure the specificity of the assay. However, the present invention contemplates methods (i.e., assays) that detect more than one species of a given genus. That is, the present invention contemplates detecting multiple members of the genus *Mycoplasma*, the genus *Acholeplasma*, the genus *Ureaplasma*, the genus *Phytoplasma* and the genus *Spiroplasma* in the same assay. Therefore, the present invention targets a genomic sequence that is well conserved among the *Mycoplasma/Acholeplasma/Ureaplasma/Phytoplasma/ Spiroplasma* for design of the present *Mycoplasma/Acholeplasma/Ureaplasma/Phytoplasma/Spiroplasma* primers. Attention was focused on genes for which sequence data was known for a majority of the species of interest. The 16S rRNA gene was selected as a suitable target. The genomic 16S rRNA gene sequences are available from GenBank via the web site of the National Center for Biotechnology Information (via hypertext transfer protocol on the world wide web at ncbi.nlm.nih.gov/Genbank/) for eight of the most common *Mycoplasma* species that infect cell cultures: *Acholeplasma laidlawii* (NCBI ID#M23932), *Mycoplasma arginini* (NCBI ID#M24579), *M. fermentans* (NCBI ID#M24289), *M. hominis* (NCBI ID#M24473), *M. hyorhinis* (NCBI ID#M24658), *M. orale* (NCBI ID#M24659), *M. pirum* (NCBI ID#M23940), *M. salivarium* (NCBI ID#M24661), and *E. coli* (NCBI ID#2367315). Additional *Mycoplasma* 16S rRNA gene sequences are also available through GenBank. The highly conserved nature of the 16S rRNA gene sequences makes it possible to design small sets of primers (e.g., 2, 3, or 4 members) that recognize multiple (e.g., 2, 3, 4, 5, 6, 7, 8, or more) *Mycoplasma/Acholeplasma/Ureaplasma/Phytoplasma/Spiroplasma* species. Although targeting this evolutionarily conserved sequence permits one to identify numerous species of *Mycoplasma/Acholeplasma/Ureaplasma/ Phytoplasma/Spiroplasma* with a limited number of primers or primer sets, because stretches of sequences within this target might be conserved across other species, primers of the invention were designed such that they serve as primers for extension of *Mycoplasma/Acholeplasma/Ureaplasma/Phytoplasma/Spiroplasma*, but not for non-target species nucleic acids, which might be present in samples being tested or in recombinant enzyme preparations that are added to the primers to create an amplification mixture.

In essence, to minimize the occurrence of false positives (i.e., detection of non-target nucleic acids that might be present in reaction mixtures), the *Mycoplasma*/Acholeplasma primers of the present invention (e.g., SEQ ID NO: 1-9) were designed so that they cannot serve as primers for extension of non-target sequences. Accordingly, the design of the *Mycoplasma/Acholeplasma* primers of the present invention avoids the amplification of any potential *E. coli* DNA contamination present in cloned DNA polymerase (e.g., Taq DNA polymerase), which is typically used for the amplification reaction.

In embodiments, the present invention provides a primer for amplification and detection of *Mycoplasma/Acholeplasma/Ureaplasma/Phytoplasma/Spiroplasma* species, which has a nucleotide sequence comprising the sequence of SEQ ID NO: 1, SEQ ID NO:2, SEQ ID NO:3, SEQ ID NO:4, SEQ ID NO:5, SEQ ID NO:6, SEQ ID NO:7, SEQ ID NO:8, or SEQ ID NO:9.

In embodiments, the primer has a nucleotide sequence that consists of the sequence of SEQ ID NO:1, SEQ ID NO:2, SEQ ID NO:3, SEQ ID NO:4, SEQ ID NO:5, SEQ ID NO:6, SEQ ID NO:7, SEQ ID NO:8, or SEQ ID NO:9.

In embodiments, the present invention provides a primer set, which comprises two or more primers for the amplification and detection of *Mycoplasma/Acholeplasma/Ureaplasma/Phytoplasma/Spiroplasma* species. The primer set can include combinations of two or more primers, each individually having a nucleotide sequence comprising the sequence of SEQ ID NO: 1, SEQ ID NO:2, SEQ ID NO:3, SEQ ID NO:4, SEQ ID NO:5, SEQ ID NO:6, SEQ ID NO:7, SEQ ID NO:8, or SEQ ID NO:9. Thus, for example, a primer set according to the present invention can comprise two primers, one having a sequence comprising SEQ ID NO: 1 and the other having a sequence comprising SEQ ID NO:2. Likewise, a primer set according to the present invention can comprise a primer having a sequence comprising SEQ ID NO: 1 and the other having a sequence comprising SEQ ID NO:4. It is to be understood that primer sets are not limited to two primers. Rather, three or more primers can be present in a set. Exemplary primers and primer sets are presented in this patent application.

In a preferred embodiment, a primer set comprising a primer having a sequence comprising SEQ ID NO: 1 and/or SEQ ID NO:3 and a primer having a sequence comprising SEQ ID NO:2 and/or SEQ ID NO:4 is provided.

Primers according to the invention can also be specific for nucleic acids from organisms other than *Mycoplasma/Acholeplasma/Ureaplasma/Phytoplasma/Spiroplasma*. That is, primers according to the invention that are useful for detecting *Mycoplasma/Acholeplasma/Ureaplasma/Phytoplasma/ Spiroplasma* species can be primers that are used to run control reactions, such as amplification controls (AC). As used herein, these are referred to as control primers.

Although the primers can have a sequence that consists of the sequences presented herein, the primers can also contain other nucleotides, as long as the additional nucleotides do not destroy the ability of the primer to serve its function or reduce the specificity of the primer. While there is no absolute length requirement for primers of the invention, suitable primers typically are between 12 and 35 nucleotides in length. For example, suitable primers are often 15 or more nucleotides in length, 22 or more nucleotides in length, 25 or more nucleotides in length, or 30 or more nucleotides in length.

Primer syntheses can be carried out by any known method. For example, primers can be produced using cyanoethyl phosphoramidite chemistry, ammonium hydroxide deprotection, and desalting by gel filtration chromatography. If desired, primers can be further purified by high performance liquid chromatography (HPLC), polyacrylamide gel electrophoresis (PAGE), or any other method known to those of skill in the art.

Nucleic acids other than primers are also part of this invention. These nucleic acids can be used as controls for monitoring various aspects of the methods of the present invention. The control nucleic acids can be *Mycoplasma/Acholeplasma/ Ureaplasma/Phytoplasma/Spiroplasma* nucleic acids, which can be used as positive controls to confirm that the methods and primers are suitable for amplification and detection of *Mycoplasma/Acholeplasma/Ureaplasma/Phytoplasma/ Spiroplasma* nucleic acids. The control nucleic acids can also be other bacterial nucleic acids or eukaryotic nucleic acids. These other nucleic acids can be used to confirm the specificity of the primers used to amplify and detect *Mycoplasma/ Acholeplasma/Ureaplasma/Phytoplasma/Spiroplasma* nucleic acids and to confirm that no inhibitors of amplification were present in the amplification mixtures. Control nucleic acids can be genomic or sub-genomic nucleic acids.

In embodiments, genomic or sub-genomic nucleic acids from *M. pirum* and/or *A. laidlawii.* are provided. These nucleic acids can be used in the methods of the invention as positive control templates to validate that polymerase-mediated amplification of *Mycoplasma/Acholeplasma* templates can be successfully detected. In other embodiments, genomic or sub-genomic nucleic acids from one or more other *Mycoplasma* and/or *Acholeplasma* are provided as positive control templates.

In embodiments, eukaryotic sub-genomic nucleic acids are provided to enable the practitioner to confirm that the methods of the invention were not inhibited by some substance, such as one present in the sample being tested. As used herein, these nucleic acids, and the amplification reactions that they participate in, are called amplification controls (AC). A non-limiting example of a suitable genomic or sub-genomic nucleic acid is nucleic acid encoding the mouse muscle nicotinic acetylcholine receptor gamma-subunit, or a portion thereof, the sequence for which is publicly available.

In other embodiments, prokaryotic nucleic acids are provided. In these embodiments, the prokaryotic nucleic acids contain sequences that are homologous to the target *Mycoplasma/Acholeplasma/Ureaplasma/Phytoplasma/Spiroplasma* sequences. These prokaryotic nucleic acids can be used to assess the specificity of the *Mycoplasma/Acholeplasma/Ureaplasma/Phytoplasma/Spiroplasma* primers. Exemplary nucleic acids for these embodiments are nucleic acids encoding all or part of the *E. coli* 16S rRNA gene.

Although the specificity of the primers can be determined using prokaryotic nucleic acids, it can also be assessed without the addition of these nucleic acids because recombinantly produced polymerases suitable for use in the present methods typically contain contaminating prokaryotic nucleic acids, which can serve as the control nucleic acid. Thus, even in the absence of addition of, for example, *E. coli* DNA, the specificity of the *Mycoplasma*/Acholeplasma primers can be determined simply by adding a recombinantly produced polymerase suitable for PCR, such as Taq polymerase.

Use of control nucleic acids, and exemplary nucleic acids are discussed in more detail below.

In a second aspect, the invention provides methods of acellular amplification of target nucleic acids. The methods of the invention use at least two oligonucleotides to specifically amplify *Mycoplasma, Acholeplasma, Ureaplasma, Phytoplasma* and/or *Spiroplasma* nucleic acids, while essentially avoiding amplification of nucleic acids from other bacteria or eukaryotes (except as specifically intended when those nucleic acids are used for control reactions). In general, the methods comprise providing a purified target nucleic acid, and amplifying and detecting target sequences within the target nucleic acid. FIGS. 1-8 show exemplary embodiments of the methods of the invention, which will be discussed below.

Purified target nucleic acids can be provided in any state of purification. However, it is preferred that the nucleic acids be provided in as purified state as possible. As with most, if not all, acellular amplification reactions, it has been found that the sensitivity and reproducibility of the methods of the present invention are improved, generally, as the purity of the target nucleic acid is increased. For example, reduction or elimination of substances present in culture media, such as those containing fetal calf serum, metabolic products, cell debris, or antibiotics, has been found to improve the results of the present methods.

Thus, in embodiments, the methods include purifying the target nucleic acid prior to amplification. Numerous suitable purification protocols for nucleic acids are known in the art. For example, the StrataPrep® PCR Purification Kit (Catalog #400771, Stratagene, La Jolla, Calif.) can be used to purify the target nucleic acid prior to amplification. Alternatively, a silica gel (e.g., StrataClean® Resin, Cat. No. 400714, Stratagene, La Jolla, Calif.) may be used to reduce the concentration of components in the sample that are inhibitory to PCR amplification. The practitioner may select any suitable protocol or modify a known protocol to optimize the amplification of the target nucleic acid sequences, based on the source of the nucleic acid, the amount of nucleic acid present in the source, or any other variable that might affect purification quality and quantity. Such modifications are well known to the skilled artisan, and can be implemented without undue or excessive experimentation.

The methods of the invention include amplifying target nucleic acids to permit detection of *Mycoplasma, Acholeplasma, Ureaplasma, Phytoplasma* and/or *Spiroplasma* infection of a sample.

It is further contemplated that other enzyme-mediated amplification assays that are known in the art can also be used in the present methods. The presence of contaminating recombinant host nucleic acid will pose the same false-positive problems in any such system that is dependent upon the extension of a hybridized primer for its signal and for its specificity.

Suitable conditions for acellular amplification reactions are known in the art and can be applied or modified by those of skill in the art to optimize reactions to achieve desired goals. Thus, variations on the exact amounts of the various reagents and on the conditions for the PCR (e.g., buffer conditions, cycling times, etc.) that lead to similar amplification or detection results are known to those of skill in the art or readily identified, and are considered to be equivalents.

Thus, in embodiments, the present invention provides a method of acellular amplification of *Mycoplasma, Acholeplasma, Ureaplasma, Phytoplasma* or *Spiroplasma* nucleic acids. The method comprises providing a sample suspected of containing a purified nucleic acid from *Mycoplasma, Acholeplasma, Ureaplasma, Phytoplasma* or *Spiroplasma*; providing at least two oligonucleotide primers, each of these primers having a sequence comprising the sequence of SEQ ID NO: 1, SEQ ID NO:2, SEQ ID NO:3, SEQ ID NO:4, SEQ ID NO:5, SEQ ID NO:6, SEQ ID NO:7, SEQ ID NO:8, or SEQ ID NO:9; amplifying the purified *Mycoplasma, Acholeplasma, Ureaplasma, Phytoplasma* or *Spiroplasma* nucleic acid; and detecting the product of the amplifying reaction. Embodiments of the methods specifically detect *Acholeplasma laidlawii, Mycoplasma arginini, M. fermentans, M. hominis, M. hyorhinis, M. orale, M. salivarium, M. pirum,* or a combination of two or more of these organisms. In embodiments, a hot-start PCR reaction is performed. In such situations, a hot start Taq DNA polymerase, such as SureStart® Taq DNA polymerase from Stratagene, can be used to improve PCR reaction by decreasing background from non-specific amplification and to increase amplification of the desired extension product.

As mentioned above, in embodiments, at least a portion of the amplification products is analyzed using gel electrophoresis. Gel electrophoresis can be used to evaluate the amplification reaction prior to amplification using single stage PCR. Gel readout can be used to optimize single stage PCR reaction parameters by permitting one to identify successful PCR conditions, and permitting one to confirm that the amplified product is the correct size. That is, the presence of an amplified band of an expected size, detected after gel electrophoresis of PCR amplification products, confirms the presence of the target bacterium or genus of target bacteria. It also permits the user to qualitatively, semi-quantitatively, or quantitatively assess the amplification reaction. In these embodiments, the results of the gel can aid the user in making suitable minor changes to the amplification reaction conditions or identify potential problems, such as insufficiently pure starting materials. Upon confirming by gel readout that amplification has successfully occurred, the user can continue with the general method of the invention by detecting amplified product, or can repeat the amplification process using the parameters that were identified as suitable for amplification. In these embodiments, gel readout is used to optimize the *Mycoplasma, Acholeplasma, Ureaplasma, Phytoplasma* and/or *Spiroplasma* detection assay.

Thus, the present invention provides a method of single stage PCR amplification and detection of target *Mycoplasma/Acholeplasma/Ureaplasma/Phytoplasma/Spiroplasma* sequences to detect infection of a sample with one or more *Mycoplasma, Acholeplasma, Ureaplasma, Phytoplasma* and/or *Spiroplasma* bacteria, where the single stage PCR amplification/detection uses SYBR® Green (Molecular Probes, Eugene, Oreg.) dye, the Brilliant® SYBR® Green QPCR Master Mix (Stratagene, La Jolla, Calif.), and, optionally, the ROX passive reference dye. The method comprises purifying nucleic acids from a sample, and performing single stage PCR with a *Mycoplasma, Acholeplasma, Ureaplasma, Phytoplasma* and/or *Spiroplasma* primer set of the invention. In embodiments, the method further comprises amplifying *Mycoplasma/Acholeplasma/Ureaplasma/Phytoplasma/Spiroplasma* control gDNA with the same primer set used to test for *Mycoplasma/Acholeplasma/Ureaplasma/Phytoplasma/Spiroplasma* in the sample being tested. In exemplary embodiments, in a separate reaction, a known amount of purified M orale control gDNA is amplified. In exemplary embodiments, in a separate reaction, a known amount of purified *A. laidlawii* gDNA is amplified. In yet other embodiments, the method comprises, in addition to performing single stage PCR with a *Mycoplasma, Acholeplasma, Ureaplasma, Phytoplasma* and/or *Spiroplasma* primer set of the invention, amplifying *Mycoplasma/Acholeplasma/Ureaplasma/Phytoplasma/Spiroplasma* control gDNA, or all of them, amplifying an amplification control (AC) template with two AC primers. In embodiments, the AC template is simultaneously amplified with the *Mycoplasma, Acholeplasma, Ureaplasma, Phytoplasma* and/or *Spiroplasma* in the sample in the same reaction tube. In other embodiments, the *Mycoplasma, Acholeplasma, Ureaplasma, Phytoplasma* and/or *Spiroplasma* sample is (are) amplified in a separate reaction tube than the AC, but under the same reaction conditions. In yet further embodiments, amplification is analyzed and, optionally, quantitated by generating a standard curve and comparing the sample results to the standard curve.

The methods of the present invention can also include monitoring or detecting amplification of target and/or control sequences using the different melting temperatures of amplification products. That is, in addition to detecting fluorescence due to dsDNA by way of an amplification plot, the presence and identify of PCR products can be monitored by assaying the dissociation of dsDNA in the reaction mixture. In general, when detecting dsDNA amplification products, samples are first denatured at high temperature, then allowed to re-anneal. They are then subjected to a stepwise increase in temperature from about 55° C. to about 95° C., with fluorescence measurement taken periodically, for sample at each temperature increment. As the temperature increases, the amplification products in each tube will melt according to their composition. If primer-dimer or nonspecific products were made during the amplification step, they will generally melt at a lower temperature (Tm) than the desired products. The melting of products results in SYBR® Green dissociation from the nucleic acids, which results in decreased fluorescence. After data collection is complete, fluorescence is plotted versus temperature. For an easy interpretation of the dissociation profile the first derivative of fluorescence should be displayed, i.e. —R'(T) or —Rn'(T).

Dissociation curves are typically generated by following the instrument manufacturer's guidelines for setting up a dissociation curve. For example, on an Mx3000P instrument (Stratagene), the positive control reaction typically produces an early Ct (~26) during amplification and a dissociation curve peak with Tm about 82° C., indicating that the experiment is working properly. The negative control reaction produces no or little Ct during amplification and no or little peaks in the dissociation curve. If a culture is contaminated with *Mycoplasma, Acholeplasma, Ureaplasma, Phytoplasma* and/or *Spiroplasma* (>10-50 cell equivalents per sample), a Ct value (<30) will typically be observed in the amplification data and the dissociation curve will include a peak at Tm around 82° C. For cell culture reactions spiked with the Amplification Control template exemplified in the present text, a Ct value (<30) should be observed in the amplification data and the dissociation curve should include a Tm peak around 85° C. Failure to obtain a Ct value and a dissociation Tm peak around 85° C. indicates that the sample may contain agents inhibitory to the PCR amplification.

In conjunction with a dissociation curve, a standard curve can be generated from single stage PCR data. The standard curve can provide information about the efficiency of amplification of the target nucleic acid, the concentration range through which linear amplification occurs in the method, and, not least importantly, the quantity of nucleic acids detected in a sample. For example, a series (e.g., serial dilutions) of known quantities of purified gDNA from an organism can be run, and single stage PCR amplification data collected. This data can then be used to generate a standard curve for detection of that DNA. A sample containing an unknown number of organisms can then be analyzed, and the number of copies of DNA detected can be determined using the standard curve. This information, coupled with information about the efficiency of isolation of DNA from the sample, can permit the user to determine the total number of organisms present in the original sample.

The methods of the invention can include providing and amplifying nucleic acids other than those of the target *Mycoplasma, Acholeplasma, Ureaplasma, Phytoplasma* and/or *Spiroplasma*. Such other nucleic acids which act as controls for the methods, and can be purified by any known technique, for example by use of any of the kits discussed above. These other nucleic acids can be used as controls to assess the specificity of the PCR reaction for *Mycoplasma/Acholeplasma/Ureaplasma/Phytoplasma/Spiroplasma*, and to detect the presence of PCR inhibitors in the sample being tested. Suitable other nucleic acids include other prokaryote nucleic acids or eukaryote nucleic acids. Controls according to the invention are of three types: a negative control, a positive control, and an amplification control (AC). Broadly, controls are methods of amplifying nucleic acids to obtain information about the performance of amplification and detection of target nucleic acids. The controls include primers for amplification reactions, and methods of amplifying nucleic acids. The controls can also include template nucleic acids that are specifically amplified by the primers. Although the methods of the invention can be performed without performing any of the controls, performing one, two, or all three of the controls can provide the practitioner with information that can be advantageous under some circumstances, such as when the method detects the presence of target nucleic acids when the practitioner did not expect such a result, when the method fails to provide the expected results, or when the method provides the expected results, but fails to provide the quality or quantity of results expected.

The first control is a negative control to confirm that the primers used for amplification and detection of *Mycoplasma/ Acholeplasma/Ureaplasma/Phytoplasma/Spiroplasma* do not amplify non-target sequences that might be present in the amplification/detection reaction mixture. The negative control reaction contains all of the reagents, primers, solutions, etc. that are present in the test reaction except the sample to be tested. Although not required by the present methods, to ensure the most valid results, the negative control reaction should be run the same way that the test reaction is run, using the same thermocycler and same amplification program. Results of the negative control reaction can be monitored in any known way. In embodiments, the results are monitored by a single stage PCR reaction. In embodiments, the results are monitored by analysis of gel electrophoresis of at least a portion of the amplification reaction mixture after amplification has been performed. In the latter method, a band on the gel indicates the presence of contaminating nucleic acids in one or more of the reagents, solutions, etc. used for the amplification reaction.

The second control is a positive control. The positive control uses a 16S rRNA gene, or portion thereof, from a *Mycoplasma, Acholeplasma, Ureaplasma, Phytoplasma* and/or *Spiroplasma* species, and an amplification protocol. This control contains sequences to which the *Mycoplasma/Acholeplasma/Ureaplasma/Phytoplasma/Spiroplasma* primers should hybridize and prime amplification of the control nucleic acid. This control is used to confirm that the *Mycoplasma/Acholeplasma/Ureaplasma/Phytoplasma/Spiroplasma* primers hybridize with the target sequences and prime amplification of the target sequences, and to confirm that amplification of target *Mycoplasma/Acholeplasma/Ureaplasma/Phytoplasma/Spiroplasma* nucleic acid can be detected by the methods of the invention. As with the other controls, although not required by the present methods, to ensure the most valid results, the positive control reaction should be run the same way that the test reaction is run, using the same thermocycler and same amplification program.

The third control is an amplification control (AC). The amplification control uses a nucleic acid from a non-target species, and at least two control primers, along with an amplification protocol. The control primers are designed to act as specific primers for amplification of the AC nucleic acid under the amplification protocol used, and to produce a double stranded product of known size, which can be detected using standard techniques. One advantage of this positive control is to reduce the occurrence of false negative results in the methods of the invention. More specifically, when the AC is run under the same conditions as the test sample, production of an amplification product of the expected size and quantity indicates that the amplification method is suitable for amplifying nucleic acids. Thus, a lack of an amplification product in the test sample indicates the lack of target nucleic acids in the sample. However, the lack of an amplification product in the AC reaction indicates that at least one inhibitor of amplification is present in the reaction mixtures, and the potential for the results for the sample being a false negative.

Various non-limiting exemplary primers and control templates are presented in FIG. 2.

The methods of the invention contemplate running the AC as a separate reaction in a separate tube from the sample reaction ("two tube format"). In this embodiment, two reactions are set up to run in parallel, in two separate reaction vessels. The methods of the invention also contemplate running the AC as a reaction in the same tube as the sample reaction ("single tube format"). In either embodiment, the AC, if amplified, will produce a double stranded nucleic acid of a known size (based on the placement of the control primers), which can be detected by any known technique, including gel electrophoresis and melting temperature, which is described in more detail below.

Accordingly, some embodiments invention include providing an amplification control nucleic acid and at least two primers that specifically hybridize to the amplification control; amplifying the amplification control; and detecting the product of the amplification control amplifying reaction. In certain embodiments, the amplifying and detecting of the purified *Mycoplasma, Acholeplasma, Ureaplasma, Phytoplasma* or *Spiroplasma* nucleic acid, and the amplifying and detecting of the amplification control are performed in a different reaction tube, while in other embodiments, the amplifying and detecting of the *Mycoplasma, Acholeplasma, Ureaplasma, Phytoplasma* or *Spiroplasma* nucleic acid and the amplifying and detecting of the amplification control are performed in the same reaction tube.

As discussed above, the methods can include monitoring or detecting amplification of target sequences and/or control sequence using a dye that detects double stranded nucleic acids to a much greater extent than single stranded nucleic acids or free nucleotides. The methods can also include monitoring or detecting amplification of target sequences and/or control sequences using other techniques, such as gel electrophoresis. Thus, the detection of the extension product in an acellular amplification (e.g., PCR or single stage PCR) may be performed by any methods described herein or known in the art, such as by polynucleotide staining or through a detectable label by using a labeled primer for the amplification.

In some embodiments, a polynucleotide stain is used due to its preferential staining for double stranded DNA. Thus the amount of extension products is reflected by the amount of stain signal produced. The use of such stains greatly decreases the cost and complexity of the reactions. The polynucleotide stain is selected to have the desired relative polynucleotide binding affinity and spectral characteristics, according to methods well known in the art. While fluorescent stains are preferred stain for the present invention, any polynucleotide stain that emits light (including chemiluminescence or phosphorescence) is also useful.

Useful polynucleotide stain may be a phenanthridinium dye, including monomers or homo- or heterodimers thereof, that give an enhanced fluorescence when complexed with polynucleotides. Examples of phenanthridinium dyes include ethidium homodimer, ethidium bromide, propidium iodide, and other alkyl-substituted phenanthridinium dyes.

Useful polynucleotide stains may be or may incorporate an acridine dye, or a homo- or heterodimer thereof, such as acridine orange, acridine homodimer, ethidium-acridine heterodimer, or 9-amino-6-chloro-2-methoxyacridine.

Useful polynucleotide stains may also be an indole or imidazole dye, such as Hoechst 33258, Hoechst 33342, Hoechst 34580 (Molecular Probes, Inc. Eugene, Oreg.), DAPI (4',6-diamidino-2-phenylindole), or DIPI (4',6-(diimidazolin-2-yl)-2-phenylindole).

Useful polynucleotide stains may also be a cyanine dye or a homo- or heterodimer of a cyanine dye that gives an enhanced fluorescence when associated with polynucleotides. Any of the dyes described in U.S. Pat. No. 4,883,867 to Lee, U.S. Pat. No. 5,582,977 to Yue et al., U.S. Pat. No. 5,321,130 to Yue et al., and U.S. Pat. No. 5,410,030 to Yue et al. may be used, including polynucleotide stains commercially available under the trademarks TOTO, BOBO, POPO, YOYO, TO-PRO, BO-PRO, PO-PRO and YO-PRO from Molecular Probes, Inc., Eugene, Oreg. Likewise, any of the dyes described in U.S. Pat. No. 5,436,134 to Haugland et al., U.S. Pat. No. 5,658,751 to Yue et al., and U.S. Pat. No. 5,863,753 to Haugland et al. may be used, including polynucleotide stains commercially available under the trademarks SYBR, SYTO, SYTOX, PICOGREEN, OLIGREEN, and RIBOGREEN from Molecular Probes, Inc. (Eugene, Oreg.).

Useful polynucleotide stains may also be a monomeric, homodimeric or heterodimeric cyanine dye that incorporates an aza- or polyazabenzazolium heterocycle, such as an azabenzoxazole, azabenzimidazole, or azabenzothiazole, that gives an enhanced fluorescence when associated with polynucleotides. This includes, but is not limited to, polynucleotide stains commercially available under the trademarks SYTO, SYTOX, JOJO, JO-PRO, LOLO, LO-PRO from Molecular Probes, Inc., (Eugene, Oreg.).

Other useful polynucleotide stains include, but are not limited to, 7-aminoactinomycin D, hydroxystilbamidine, LDS 751, selected psoralens (furocoumarins), styryl dyes, metal complexes such as ruthenium complexes, and transition metal complexes (incorporating $Tb^{3+}$ and $Eu^{3+}$, for example).

A preferred stain used in some embodiments of the invention is SYBR® Green I, which is commercially available from Molecular Probes Inc., Eugene, Oreg.

In a preferred embodiment, a passive reference dye is optionally used to normalize for non-amplification related fluorescence signal variation. A passive reference dye does not take part in the amplification reaction and its fluorescence remains constant during the reaction. The passive reference dye, therefore, provides an internal reference to which the amplification related signal can be normalized during data analysis. This is useful to correct for fluorescent fluctuations due to changes in concentration or volume in the wells. Normalization using passive reference dye is known in the art and it can be accomplished using appropriate analysis software, which divides the emission intensity of the reporter dye (e.g., a polynucleotide stain) by the emission intensity of the passive reference to obtain a ratio defined as the Rn (normalized reporter) for a given reaction well. The difference between the Rn value of a reaction containing all components including the template (Rn+), and the Rn value of an unreacted sample (i.e., no production of extension product, Rn−) equals the ΔRn value, which reliably indicates the magnitude of the signal generated by the given set of PCR conditions.

In one embodiment, ROX passive reference dye is used in addition to a polynucleotide stain (e.g., SYBR® Green). The excitation and emission wavelengths of the reference dye are 584 nm and 612 nm, respectively. The ROX dye can be provided as a concentrated solution dissolved in a buffer that is compatible with the PCR reaction buffer. The amount of the ROX passive reference dye can be adjusted based on the particular requirements of different instruments. In a preferred embodiments SYBR® Green I is used to stain the extension product and ROX passive reference dye is used to normalize the signal generated by SYBR® Green. It is recommended that the use of ROX passive reference dye follows guidelines for passive reference dye optimization for each instrument used. For Stratagene's Mx3000P or Mx4000 instruments, ROX passive reference dye can be used at a final concentration of 30 nM according to one embodiment. For ABI real-time fluorescence detection platforms, such as the PRISM 7700 or the GeneAmp 5700, ROX passive reference dye can be used at a final concentration of 300 nM according to another embodiment. In one embodiment, for instruments that allow excitation at ~584 nm (including most tungsten/halogen lamp-based instruments and instruments equipped with a ~584 nm LED), optimization can begin by using the reference dye at a final concentration of 30 nM. In another embodiment, for instruments that do not allow excitation near 584 nm, (including most laser-based instruments), optimization can begin by using the reference dye at a final concentration of 300 nM.

SYBR® Green I dye has a high binding affinity to the minor groove of double-stranded DNA (dsDNA). It has an excitation maximum at 497 nm and an emission maximum at 520 nm. In the unbound state the dye exhibits little fluorescence; however, when bound to dsDNA, the fluorescence greatly increases, making it useful for the detection of product accumulation during PCR. More specifically, during the denaturation step of PCR, all DNA becomes single-stranded. At this stage, SYBR® Green is free in solution and produces little fluorescence. During the annealing step, the primers will hybridize to the target sequence, resulting in dsDNA to which SYBR® Green I can bind. As the PCR primers are extended in the elongation phase, more DNA becomes double-stranded (e.g., as extension products), and a maximum amount of SyBR® Green I is bound. The increase in fluorescence signal intensity depends on the initial concentration of target present in the PCR reaction.

One consideration when using SYBR® Green I, however, is that signal can also be generated from nonspecific dsDNA (e.g., primer-dimers (PD) and spurious PCR products). The fluorescence resulting from amplification of the target will not be initially distinguishable from fluorescence attributable to the spurious PCR products. To distinguish between fluorescence derived from specific and non-specific products, the present method contemplates embodiments comprising a dissociation curve. During the dissociation curve, dsDNA is melted into ssDNA, for example by a stepwise increase in temperature or a linear increase in temperature, with fluorescence data collected at each step or continuously through the linear increase in temperature. The dissociation curve fluorescence data is analyzed to reveal the temperature(s) at which major populations of dsDNA are converted to ssDNA (i.e., the major Tm peaks). For example, the *Mycoplasma* amplicons amplified using the primers according to one embodiment of the present invention have a Tm of ~82° C. In contrast, fluorescence due to PD displays a Tm of <75° C. (e.g., 74° C.), and spurious PCR products typically show a broad Tm.

Note that a common problem in SYBR® Green QPCR is the formation of primer dimers. Primer dimers (PD) derive from primers in a reaction that anneal and can be extended in PCR. The extended PD bind SYBR® Green and produce a signal. The dissociation curve of the present invention aids the practitioner in evaluating if PD are present in the reaction. PD typically melt at a lower temperature than the bona fide product, and thus can be distinguished from the product. Typical dissociation curves of the present invention (when target *Mycoplasma* nucleic acids are present in a sample) will contain a major peak for the *Mycoplasma* target at about 82° C. They will also contain a major peak at a higher temperature (Tm of about 85° C.), corresponding to the amplification control (AC). If a third peak is present, it will typically be a minor peak at about 74° C., representing PD. The absence of a Tm peak around 74° C. generally indicates the absence of primer dimers.

One problem encountered when laboratories routinely use the same primer sets for assays, such as the *Mycoplasma* detection assays described herein, is that small amounts of the amplified products from previous assays can contaminate subsequent reactions, giving false positive results. To avoid this problem, the *Mycoplasma* detection assays described herein can be routinely carried out in the presence of dUTP, which permits the user to eliminate carry-over PCR products with uracil DNA-glycosylase (UDG). In the event that amplification product is inadvertently carried over from one experiment to another, the enzyme UDG will catalyze the release of free uracil found in the contaminating product and hydrolysis of the DNA strand. A pre-incubation of the PCR reaction for 10 minutes at 37° C. activates the UDG enzyme. Heat energy in a subsequent denaturation step (e.g., 10 minutes at 94° C.) eliminates the UDG activity, activates the DNA polymerase (if modified for "hot-start" activation, e.g., SureStart® Taq), and catalyzes the cleavage of the contaminating abasic phosphodiester backbone. UDG is commercially available, e.g., from New England Biolabs (Cat. # M0280S).

The methods of the invention provide high specificity of PCR-based bacterial assays. More specifically, the methods have a very low frequency of false positive results. A common source of false positive results in PCR-based bacterial assays that use recombinant polymerase is the recombinant polymerase, which is often contaminated with genomic DNA from the host bacterium (typically *E. coli*). When the host bacterium has a homologous sequence to the target gene sequence in the bacterial genus or species being detected, the use of recombinant preparations of recombinant polymerase, for example Taq polymerase, often results in false positive amplification results when the primers cross-hybridize and permit extension from contaminating host species genomic DNA template.

The high specificity (i.e., lower false positive rates) of the present methods is achieved, at least in part, by the selection of PCR primer sequences that will not result in extension of the primer even if the primer, as a whole, can hybridize with contaminating template nucleic acid from the recombinant polymerase host species or other contaminating nucleic acids. In general, primer sequences are selected to have at least the 3' terminal nucleotide of the primer mismatched with the *E. coli* genomic sequence that is homologous with the *Mycoplasma, Acholeplasma, Ureaplasma, Phytoplasma* or *Spiroplasma* target sequence. In this way, extension of the primer from any contaminating *E. coli* nucleic acids is minimized or eliminated, thus reducing or eliminating non-specific amplification of non-target nucleic acids (and thus false positive results).

It is also noted that the present methods can be used whenever a recombinant enzyme produced in bacteria, including a non-polymerase recombinant enzyme, is used in a mixture that is ultimately subjected to a PCR amplification of a target gene sequence from a different bacterial species. Thus, if, for example, a recombinant uracil DNA glycosylase or other recombinant enzyme is used in treatment or pre-treatment of a sample to be subjected to amplification, this approach will avoid false positive signal from recombinant host nucleic acid introduced with that recombinant enzyme.

In a third aspect, the invention provides compositions. In general, the compositions comprise at least two oligonucleotide primers that can be used to specifically amplify *Mycoplasma, Acholeplasma, Ureaplasma, Phytoplasma* and/or *Spiroplasma* nucleic acids. The compositions can also contain some or all of the reagents, solvents, and other nucleic acids for practicing the methods of the invention. The compositions can also include primers for performing control reactions. Likewise, the compositions can comprise genomic or sub-genomic nucleic acids that are suitable for use as control templates. Thus, in embodiments, compositions of the invention comprise at least one *Mycoplasma* specific primer and at least one *Mycoplasma* gDNA. Other embodiments include nucleic acids for the AC aspect of the invention. Accordingly, the compositions of the invention can contain a primer set for amplification of *Mycoplasma/ Acholeplasma/ Ureaplasma/Phytoplasma/Spiroplasma* target sequences, positive control *Mycoplasma/Acholeplasma/Ureaplasma/ Phytoplasma/Spiroplasma* nucleic acids, a primer set for amplification of the control (e.g., unrelated nucleic acid sequence).

Thus, in embodiments, the composition comprises at least one oligonucleotide primer, each of these primers having a sequence comprising the sequence of SEQ ID NO: 1, SEQ ID NO:2, SEQ ID NO:3, or SEQ ID NO:4. For example, the composition can comprise a primer having a sequence comprising SEQ ID NO: 1 and a primer having a sequence comprising SEQ ID NO:2. The composition can further comprise a primer having a sequence comprising SEQ ID NO:3, a primer having a sequence comprising SEQ ID NO:4, a primer having a sequence comprising SEQ ID NO:5 and/or any other nucleic acid of this invention. Likewise, the composition can further comprise an amplification control nucleic acid and at least one oligonucleotide primer specific for the amplification control nucleic acid. It also can further be comprising Taq polymerase and/or a dye that can specifically detect double stranded DNA, such as SYBR® Green I (Molecular Probes, Eugene, Oreg.).

In a fourth aspect, the invention provides kits for detecting *Mycoplasma, Acholeplasma, Ureaplasma, Phytoplasma* and/or *Spiroplasma* species in a sample. In its most basic form, the kit of the invention can comprise one or more nucleic acids or compositions according to the invention. The kits can comprise the components in a single package or in more than one package within the same kit. Where more than one package is included within a kit, each package can independently contain a single component or multiple components, in any suitable combination. As used herein, a combination of two or more packages or containers in a single kit is referred to as "in packaged combination". The kits and containers within the kits can be fabricated with any known material. For example, the kits themselves can be made of a plastic material or cardboard. The containers that hold the components can be, for example, a plastic material or glass. Different containers within one kit can be made of different materials. In embodiments, the kit can contain another kit within it. For example, the kit of the invention can comprise a kit for purifying nucleic acids.

In general, the kits can comprise, in a single package or in packaged combination, two or more oligonucleotide primers, reagents and/or other components for performing the methods of the invention, nucleic acid templates for use as positive controls or specificity controls, or combinations of two or more of these.

In one of the embodiments, the kit according to the invention comprises at least two primers, where each of the primers has a sequence comprising SEQ ID NO: 1, SEQ ID NO:2, SEQ ID NO:3, SEQ ID NO:4, SEQ ID NO:5, SEQ ID NO:6, SEQ ID NO:7, SEQ ID NO:8, or SEQ ID NO:9., where each primer present in the kit has a sequence that differs from each other primer sequence in the kit. In embodiments, the kit comprises two primers, one comprising the sequence of SEQ ID NO: 1 and the other comprising the sequence of SEQ ID NO:2. In other embodiments, the kit comprises three primers, one comprising the sequence of SEQ ID NO: 1, the second comprising the sequence of SEQ ID NO:2, and the third primer comprising the sequence of SEQ ID NO:3, SEQ ID NO:4, or SEQ ID NO:5 and so on. In an exemplary embodiment, the kit comprises a primer comprising the sequence of SEQ ID NO: 1, a primer comprising the sequence of SEQ ID NO:2, a primer comprising the sequence of SEQ ID NO:3, and a primer comprising the sequence of SEQ ID NO:4. In yet another exemplary embodiment, the kit comprises a primer comprising the sequence of SEQ ID NO: 1, a primer comprising the sequence of SEQ ID NO:2, a primer comprising the sequence of SEQ ID NO:3, a primer comprising the sequence of SEQ ID NO:4, and a primer comprising the sequence of SEQ ID NO:5. In certain embodiments, all of the primers provided in the kit are provided in a single container, whereas in other embodiments, they are provided in at least two separate containers, alone or in combination with one or more other primer. In a specific embodiment, the kit can comprise a set of two or more, and preferably four or five, primers as described herein that recognize and amplify a 16S rRNA gene sequence from at least eight *Mycoplasma/Acholeplasma* species.

Accordingly, in embodiments, the invention provides a kit comprising at least one container holding a composition comprising at least one oligonucleotide primer, each of these primers having a sequence comprising the sequence of SEQ ID NO:1, SEQ ID NO:2, SEQ ID NO:3, SEQ ID NO:4, SEQ ID NO:5, SEQ ID NO:6, SEQ ID NO:7, SEQ ID NO:8, or SEQ ID NO:9. For example, the kit can comprise a container containing a primer having a sequence comprising SEQ ID NO:1, and a container containing a primer having a sequence comprising SEQ ID NO:2. Likewise, other containers can be provided that contain a primer having a sequence comprising SEQ ID NO:3, a primer having a sequence comprising SEQ ID NO:4, and a primer having a sequence comprising SEQ ID NO:5 and so on. Alternatively, two or more primers can be contained in one container, the invention not being limited by any particular combination of primers in each container.

The kit of the invention can comprise primers for the amplification control (AC). In embodiments, the AC primers are contained in a container separate from the other components of the kit. In other embodiments, the AC primers are contained in the same container as the *Mycoplasma/Acholeplasma/Ureaplasma/Phytoplasma/Spiroplasma* primers. In embodiments, the AC primers are contained in the same container as the AC template nucleic acid. In one embodiment, the AC primers, the AC template nucleic acid, and at least one *Mycoplasma/Acholeplasma/Ureaplasma/Phytoplasma/Spiroplasma* primer are contained in the same container.

The kit of the invention can comprise purified *Mycoplasma, Acholeplasma, Ureaplasma, Phytoplasma* and/or *Spiroplasma* nucleic acids. These nucleic acids can be genomic or sub-genomic nucleic acids. In exemplary embodiments, the kits comprise a container containing purified *Mycoplasma, Acholeplasma, Ureaplasma, Phytoplasma* and/or *Spiroplasma* gDNA. In embodiments, a known amount of *Mycoplasma* gDNA is contained in a single container within the kit. In embodiments, a known amount of *Acholeplasma* gDNA is contained in a single container within the kit. In embodiments, a known amount of *Ureaplasma* gDNA is contained in a single container within the kit. In embodiments, a known amount of Phytoplasma gDNA is contained in a single container within the kit. In embodiments, a known amount of *Spiroplasma* gDNA is contained in a single container within the kit.

In certain cases, two containers, each containing one or the other of *Mycoplasma* or *Acholeplasma* gDNA, are included in the kit. In certain cases, two containers, each containing one or the other of *Mycoplasma, Acholeplasma, Ureaplasma, Phytoplasma* and/or *Spiroplasma* gDNA, are included in the kit.

In certain other cases, a *Mycoplasma* gDNA and an *Acholeplasma* gDNA are included in a single container within the kit. In certain other cases, a *Mycoplasma*, an *Acholeplasma, Ureaplasma, Phytoplasma* and/or *Spiroplasma* gDNA are included in a single container within the kit. In embodiments, *M. orale* and *A. laidlawii* gDNA are provided in the kit, either in separate containers or together in a single container.

As mentioned above, the kit can comprise AC target nucleic acid. The AC target nucleic acid can be contained in a container separate from the other components of the kit, or in combination with one or more components. In embodiments, the AC target is contained in the same container as the AC primers. In embodiments, the AC target is contained in the same container as one or more of the *Mycoplasma* primers of the invention. The AC target nucleic acid can be any nucleic acid that comprises a sequence that can be amplified under the conditions used to amplify the target *Mycoplasma/Acholeplasma/Ureaplasma/Phytoplasma/Spiroplasma* sequence. Thus, it can be genomic or sub-genomic DNA.

The kit of the invention can comprise one or more components useful for amplifying the *Mycoplasma/Acholeplasma/Ureaplasma/Phytoplasma/Spiroplasma* target sequences. In embodiments, some or all of the reagents and supplies necessary for performing PCR are included in the kit. In exemplary embodiments, some or all reagents and supplies for performing PCR are included in the kit. Non-limiting examples of reagents are buffers (e.g., a buffer containing Tris®, HEPES® and the like), salts, and a template-dependent nucleic acid extending enzyme (such as a thermostable enzyme, such as Taq polymerase), a buffer suitable for activity of the enzyme, and additional reagents needed by the enzyme, such as dNTPs, dUTP, and/or a UDG enzyme. In embodiments, the kit comprises Brilliant®SYBR® Green QPCR Master Mix (Catalog #600548, Stratagene, La Jolla, Calif.). A non-limiting example of supplies is reaction vessels (e.g., microcentrifuge tubes).

The kit can comprise at least one dye for detecting nucleic acids, including, but not limited to, dsDNA. In embodiments, the kit comprises a sequence-non-specific dye that detects dsDNA, such as SYBR® Green dye (Molecular Probes, Eugene, Oreg.). The dye is preferably contained alone in a container. In embodiments, the dye is provided as a concentrated stock solution, for example, as a 50× solution. In embodiments, the kit comprises a passive reference dye. In these embodiments, the passive reference dye can be included in the kit alone in a separate container. The passive reference dye can be provided as a concentrated stock solution, for example, as a 1 mM stock solution. A non-exclusive exemplary passive reference dye is ROX dye. In embodiments, the kit contains either a DNA-detecting dye or a passive reference dye. In other embodiments, the kit contains both a DNA-detecting dye and a passive reference dye.

The kit can also comprise one or more components useful for purifying nucleic acids. In embodiments, these components are particularly suited for purifying *Mycoplasma/Acholeplasma/Ureaplasma/Phytoplasma/Spiroplasma* nucleic acids from eukaryotic cell cultures. The components can be, among other things, reagents and supplies that can be used to purify nucleic acids. Non-limiting examples of such reagents and supplies include, but are not limited to, a DNA binding solution, a wash buffer, and containers, such as microcentrifuge tubes, for collection of binding solutions, wash buffers, and purified nucleic acids. The components can also contain a resin, gel, or other substance that is useful for purifying nucleic acids. In embodiments, the kit comprises the components of the StrataPrep® PCR Purification Kit (Catalog #400771, Stratagene, La Jolla, Calif.).

Thus, in embodiments, the kit according to the invention can comprise in packaged combination: 1) a primer set that comprises five *Mycoplasma* primers, one each comprising the sequence of SEQ ID NO:1, SEQ ID NO:2, SEQ ID NO:3, SEQ ID NO:4, SEQ ID NO:5, SEQ ID NO:6, SEQ ID NO:7, SEQ ID NO:8, or SEQ ID NO:9.; 2) *Mycoplasma orale* gDNA; 3) *Acholeplasma laidlawii* gDNA; 4) a primer set for an AC that comprises two AC primers, one each comprising the sequence of a specific sequence; 5) an AC template that comprises genomic or sub-genomic sequences of amplification control nucleic acid sequence; 6) a Brilliant® SYBR® Green QPCR Master Mix; 7) a ROX dye solution; and 8) all of the reagents and supplies necessary for the preparation of the template and for the PCR.

In one embodiment, the invention is directed to A method of detecting contaminating cells in a specimen, the method comprising:
(a) performing a multiplex polymerase chain reaction, wherein a plurality of DNA fragments representing a plurality of contaminating cells from organisms are amplified by a plurality of forward and reverse primers,
(b) determining that a specimen is positive for the contaminating cells if a number of amplified fragments is sufficient to detect the contaminating cells in the specimen.

In a preferred embodiment, the contaminating cells are specific for *Mycoplasma, Acholeplasma, Ureaplasma, Phytoplasma* and *Spiroplasma* species.

In a preferred embodiment, the plurality of primers is selected from the group consisting of NO: 1, SEQ ID NO:2, SEQ ID NO:3, SEQ ID NO:4, SEQ ID NO:5, SEQ ID NO:6, SEQ ID NO:7, SEQ ID NO:8, and SEQ ID NO:9

In a more preferred embodiment, the primers comprise the following characteristics:
(a) about twenty to thirty bases long;
(b) melting temperature of about 60° C.;
(c) GC content of about fifty percent;
(d) minimal dimer formation; and
(e) low frequency of mutations in the primer binding site In one embodiment, the invention is directed to a method for detecting *Mycoplasma* in a specimen, the method comprising:
(a) performing a multiplex polymerase chain reaction, wherein a first set of primers amplify a first set of DNA fragments from a *Mycoplasma* genomic sequence and a second set of primers amplify a second set of DNA fragments from a *Mycoplasma* genomic sequence that are internal to the first set of DNA fragments; and
(b) determining that a specimen is positive for *Mycoplasma* if a number of amplified fragments is sufficient to detect the *Mycoplasma* in the specimen.

In one embodiment, the invention is directed to a method for detecting *Mycoplasma* in a specimen, the method comprising:

(a) performing a multiplex polymerase chain reaction, wherein
(i) a first DNA fragment comprising a *Mycoplasma* genomic sequence is amplified by a first primer pair and an internal segment of the first DNA fragment is amplified by a second primer pair,
(ii) a second DNA fragment from a *Mycoplasma* genomic sequence is amplified by a third primer pair and an internal segment of the second DNA fragment is amplified by a fourth primer pair; and
(b) determining that a specimen is positive for *Mycoplasma* if a number of amplified fragments is sufficient to detect the *Mycoplasma* in the specimen.

In a preferred embodiment, the multiplex polymerase chain reaction with the first set of primers is performed separately from the multiplex polymerase chain reaction with the second set of primers.

In a more preferred embodiment, the first set of primers and the second set of primers amplify more than one fragment representing one or more contaminating cells from a number of sequences from a number of organisms.

In a more preferred embodiment, the primer pairs are selected from the group consisting of NO: 1, SEQ ID NO:2, SEQ ID NO:3, SEQ ID NO:4, SEQ ID NO:5, SEQ ID NO:6, SEQ ID NO:7, SEQ ID NO:8, and SEQ ID NO:9.

In a more preferred embodiment, wherein the multiplex polymerase chain reaction is performed with an isolated bacterial DNA.

In a more preferred embodiment, the bacterial DNA is isolated from a clinical sample.

In a more preferred embodiment, the multiplex polymerase chain reaction is performed directly with a biological sample.

In one embodiment, the invention is directed to a diagnostic kit to detect a contaminating cell in a specimen comprising:
(a) a plurality of primers to amplify a plurality of DNA fragments representing a plurality of sequences in a number of organisms; and
(b) reagents to perform a multiplex polymerase chain reaction.

In a more preferred embodiment, the plurality of primers comprise a first set of primers to amplify a first set of DNA fragments, a second set of primers to amplify a second set of DNA fragments.

In a more preferred embodiment, the contaminating cells are selected from the group consisting of *Mycoplasma, Acholeplasma, Ureaplasma, Phytoplasma* and *Spiroplasma* species.

In a more preferred embodiment, the reagents comprise a DNA polymerase, nucleotides, and buffers. In a more preferred embodiment, wherein the first and second set of primers comprise a plurality of DNA molecules comprising of NO: 1, SEQ ID NO:2, SEQ ID NO:3, SEQ ID NO:4, SEQ ID NO:5, SEQ ID NO:6, SEQ ID NO:7, SEQ ID NO:8, and SEQ ID NO:9.

In a more preferred embodiment, wherein the reagents comprise:
(a) a buffer comprising 10 mM Tris-HCl (pH 8.3), 50 mM KCl, 1.6 mM MgCl2, 0.001% (weight/volume) gelatin; and
(b) 0.3 mM of each deoxynucleotide.

In a more preferred embodiment, wherein the primers have a concentration of about 0.05 μM.

In a preferred embodiment, the invention is directed an isolated nucleic acid segment wherein said segment includes a contiguous sequence having the sequence of or complement to a sequence that is selected from the group consisting of SEQ ID NO:1, SEQ ID NO:2, SEQ ID NO:3, SEQ ID NO:4, SEQ ID NO:5, SEQ ID NO:6, SEQ ID NO:7, SEQ ID NO:8, and SEQ ID NO:9. In a preferred embodiment, the isolated nucleic acid segment further defined as comprising a contiguous nucleic acid sequence of SEQ ID NO: 1 or its complement. In a preferred embodiment, the isolated nucleic acid segment further defined as comprising a contiguous nucleic acid sequence of SEQ ID NO:2 or its complement. In a preferred embodiment, the isolated nucleic acid segment, further defined as comprising a contiguous nucleic acid sequence of SEQ ID NO:3 or its complement. In a preferred embodiment, the isolated nucleic acid segment further defined as comprising a contiguous nucleic acid sequence of SEQ ID NO:4 or its complement. In a preferred embodiment, the isolated nucleic acid segment further defined as comprising a contiguous nucleic acid sequence of SEQ ID NO:5 or its complement. In a preferred embodiment, the isolated nucleic acid segment further defined as comprising a contiguous nucleic acid sequence of SEQ ID NO:6 or its complement. In a preferred embodiment, the isolated nucleic acid segment further defined as comprising a contiguous nucleic acid sequence of SEQ ID NO:7 or its complement. In a preferred embodiment, the isolated nucleic acid segment further defined as comprising a contiguous nucleic acid sequence of SEQ ID NO:8 or its complement. In a preferred embodiment, the isolated nucleic acid segment further defined as comprising a contiguous nucleic acid sequence of SEQ ID NO:9 or its complement.

In one embodiment, the invention is directed to an isolated nucleic acid segment, comprising a contiguous nucleic acid sequence of between about 15 and 100 bases in length, wherein said contiguous sequence has the sequence or the complement of the sequence of the same length of SEQ ID NO:1, SEQ ID NO:2, SEQ ID NO:3, SEQ ID NO:4, SEQ ID NO:5, SEQ ID NO:6, SEQ ID NO:7, SEQ ID NO:8, and SEQ ID NO:9.

In one embodiment, the invention is directed to a method using probes (fragments and/or oligonucleotides) and/or amplification primers which are specific, ubiquitous and sensitive for determining the presence and/or amount of nucleic acids from bacterial species selected from the group consisting of *Mycoplasma, Acholeplasma, Ureaplasma, Phytoplasma* and *Spiroplasma* in a any sample suspected of containing said bacterial nucleic acid, wherein said bacterial nucleic acid or variant or part thereof comprises a selected target region hybridizable with said probes or primers; said method comprising the steps of contacting said sample with said probes or primers and detecting the presence and/or amount of hybridized probes and/or amplified products as an indication of the presence and/or amount of said bacterial species.

In a preferred embodiment, the method further using probes (fragments and/or oligonucleotides) and/or amplification primers which are universal and sensitive for determining the presence and/or amount of nucleic acids from any bacteria from any sample suspected of containing said bacterial nucleic acid, wherein said bacterial nucleic acid or variant or part thereof comprises a selected target region hybridizable with said probes or primers; said method comprising the steps of contacting said sample with said probes or primers and detecting the presence and/or amount of hybridized probes and/or amplified products as an indication of the presence and/or amount of said any bacteria.

In a more preferred embodiment, the method according to this invention is performed directly on a sample obtained from cell cultures, human patients, animals, environment or food. In a more preferred embodiment, the method according to this invention is performed directly on a sample consisting of one or more bacterial colonies. In a more preferred embodiment, the method according to this invention wherein the bacterial nucleic acid is amplified by a method selected from the group consisting of: a) polymerase chain reaction (PCR), b) ligase chain reaction, c) nucleic acid sequence-based amplification, d) self-sustained sequence replication, e) strand displacement amplification, f) branched DNA signal amplification, g) nested PCR, h) an array-based amplification, and i) multiplex PCR. In a preferred embodiment, the invention is directed to a diagnostic kit for the simultaneous detection and quantification of nucleic acids of any combination of the bacterial species defined in claim 1, comprising any combination of the primers to the nucleic acid as defined in any one of SEQ ID NOs: 1-9 in whole or in part.

EXAMPLES

Various embodiments of the invention will now be described by way of a number of examples. The examples are presented solely to further describe certain embodiments of the invention, and are not to be construed as limiting the invention in any way.

Example 1

Materials and Methods

1. *Mycoplasma*.

The Mollicute strains were obtained from the American Type Culture Collection (ATCC. Mannassas, Va.) and cultured as described by the manufacturer (Table 1). Once the culture reached the desired growth, the Mollicutes were harvested for genomic DNA extraction or were used as PCR templates.

2. Cell Lines.

Several cell lines naturally infected with various *Mycoplasma* species were used for detection of *Mycoplasma*. K-562 and LoVo cell lines were also obtained by ATCC and used as negative controls (Table 2). The same noninfected cell lines were also spiked with known concentrations of colony forming units (cfu) for several *Mycoplasma* and *Acholeplasma* species in order to assess the detection sensitivity of the described method. The cell lines were cultured as described by the manufacturer (Table 2) and were maintained in a 7.5% $CO_2$ incubator. All the infected cell lines were grown and maintained in isolation and separate from the noninfected cells.

3. Primers

Two sets of primers were designed and used in this study. The designed primer amplifies the intragenic region between 16S and 23S rRNA genes. Primers F-180 and R-666 are consensus primers designed for amplification of the majority of *Mollicute* species described in Table 1. Primers A-33-F and A-715R are designed to amplify the intragenic 16S-23SrRNA region for the *Acholeplasma* species. All the primers were used at a final concentration of 0.8 µM per PCR assay.

The sequence of the primers is as follows:
Primers for Detection of 49 *Mollicute* Species

```
                                              (SEQ ID No: 1)
F 180-3    5' - GTG AAT ACG TTC TCG GRT YTTG - 3'

(SEQ ID No: 2)
R 666-3    5' - ATC GCA GRT WAG CAC GTC CTT C - 3'

(SEQ ID No: 3)
33F        5' - AAC GCC GGT GGC CTA AC - 3'

(SEQ ID No: 4)
715R       5' - CTT CAA ACG GGA TTC CAC GT - 3'
```

Primers for Detection of Eight Most Common *Mollicute* Species:

```
                                              (SEQ ID No: 5)
AL-F:
5' - AAG GTT AAG GAA CAA AGG GCA CAC AG - 3'

(SEQ ID No: 6)
AL-R:
5' - ATG GTC CTC CTA TCT TCA AAC GGG - 3'

(SEQ ID No: 7)
M7-F:
5' - TCG TAA CAA GGT ATC CCT ACG AGA ACG - 3'

(SEQ ID No: 8)
M7-R1:
5' - TTA GTA TTT AGC CTT ACC GGG TGG - 3'

(SEQ ID No: 9)
M7-R2:
5' - ACT AGT ATT TAG GCT TAC CCA ATG G - 3'
```

4. Template Preparation

Templates for PCR consisted of several types such as purified *Mycoplasma* DNA, crude *Mycoplasma* stocks, cell pellets or supernatants of various cell lines either infected or not infected with *Mycoplasma*, lysates of mixes of cell lines and *Mycoplasma* stocks. Genomic *Mycoplasma* DNA was prepared using the STAT-60 for DNA extraction (Tel-Test B Inc, Texas).

The preparation of the template was made by resuspending pellets of cell lines or mixes of cell lines and *Mycoplasma* stocks, in 50 µl of lysis buffer containing 0.5% IGEPAL CA-630, 40 mM Tris-acetate pH8.3, 1 mM EDTA pH8.0 and 230 µg/ml Proteinase K (Sigma, Mo.). The lysates were incubated at 37° C. for 10 min and then at 95° C. for an additional 10 min. When cell culture supernatants were used, 25 ml of supernatant were mixed with the same volume of lysis buffer and processed as described above.

5. PCR Conditions

Reactions were conducted in 50 µl. The reaction mixtures were prepared and aliquoted prior to the addition of the template. The following reaction mixture was made for each reaction:

| Template | 5 µl. |
| --- | --- |
| 2X PCR mix | 25 µl. |
| Hot Start Taq Polymerase | 2.5 U |
| Primers | 2 µl. |
| Internal Control | 1 µl. |
| Reaction volume | 50 µl. |

| Cycling conditions: | | |
| --- | --- | --- |
| Denaturing and activation of Taq Polymerase: | 95° C. | 4 min. |
| Cycling: | 95° C. | 15 sec |
|  | 60° C. | 30 sec |
|  | 72° C. | 30 sec |
| Number of Cycles: | | 35 |

The PCR products were analyzed using 3% NuSieve Agarose Gels. The results were recorded using the Bio-Rad Gel Doc system.

7. Speciation

For species identification of *Mycoplasma* amplicons, the PCR products were analyzed by endonuclease restriction digest analyses. Four endonucleases were used for the analyses; Ase I, Rsa I, Sau3A I and Ssp I. After 1-2 hours of incubation at 37° C. the templates were analyzed by gel electrophoresis as described above. Identification of *Mycoplasma* is based upon the pattern of restriction digest generated by each of the endonucleases. A summary of the fragments generated as result of endonuclease restriction digestion from the PCR amplicons of the eight most common *Mycoplasma* species, is provided in Table 3.

8. Hoechst and Direct Culture Testing.

Results

Primer Design and Validation.

After primer design, preliminary analysis was conducted to determine that the selected primers recognize and amplify the genomic region of Mollicutes described in Table 1. Alignments of the selected primers with published *Mycoplasma* sequences showed that these primers contained similar sequences with most of the *Mycoplasma* species published and that the position and the sequence of the wobble bases was critical for a strong hybridization of the primers against the majority of *Mycoplasma* species with confirmed sequences of 16S-23S rRNA intergenic region (ITS). With exception of *Acholeplasmas* that are known to contain two copies of 16S-23S operons, a single product in the range of 350 bp-800 bp was generated. When *Acholeplasma granularium, Acholeplasma laidlawii* and *Acholeplasma oculi* were used as templates for PCR, two amplicons of size 682 bp and 904 bp were produced. FIG. 1 shows amplification of *Mycoplasma* templates for eight *Mycoplasma* species. The size of the PCR products corresponds to the size of the intergenic region that the primers were designed to amplify. As shown, unspecific amplicons were not detected. The same type of analyses was conducted for all the remaining Mollicutes used in this study. The size of the amplicons generated for each template, is also summarized in Table 1.

To test for possibilities of unspecific hybridization of the designed primers against DNA background of host organisms, $10^6$ and $10^5$ cell lines originated from XX different organism were tested (FIG. 2). As shown, no amplification product was detected when *Mycoplasma* templates were not present. Additional cell lines of human mouse and rat were also tested and no unspecific amplification was observed. Table 4 shows a list of all the cell lines used for these analyzes.

A 150 bp DNA fragment containing on its 5' and 3' end sequences identical to one of the primer sets selected for the assay, was cloned in a pUC19 vector and used as an internal control. The size of the amplicon generated by the internal control construct is smaller that any of the amplicons generated by the amplification of the 16S-23S intergenic region of the mycoplasma genomes. As such, the internal control would always amplify with a greater efficiency ensuring the presence of the internal control in the assay. The concentration of the internal control was determined such that it would not compete with the detection of 10-100 copies of *Mycoplasma* genome. (FIG. 3).

The criteria for an effective PCR are, sensitivity and specificity of the template amplification. The lower the annealing temperature, the greater the sensitivity of the detection of the template. Low annealing temperatures on the other hand may increase the unspecific hybridization of the primers and therefore may increase the background noise and thus reduce the specificity of the assay. The optimal annealing temperature for amplification of *Mycoplasma* DNA was determined by evaluating the efficiency of the PCR while applying a temperature gradient during the annealing step. While the best amplification conditions were obtained for annealing temperature between 58° C. and 62° C., a 60° C. temperature was chosen for the annealing step (data not shown).

Specificity of the Assay in the Presence of Background Cells and *E Coli*

Once the primers, internal control and the PCR buffer condition were selected, the assay, in its final conditions was tested for its performance as well as background noise. Several cell lines as described in Table 4 were used for this assay as well as several species of prokaryotes, fungi and yeast are more often found in cell culture contaminants. While some amplification of *E. coli* was observed (FIG. 4), the lowest concentration of *E. coli* needed to generate an amplicon, $10^5$-$10^4$ cells, is high enough to produce turbulence and other visible changes in the cell culture, and is therefore unlikely to be used for further studies and tests, including the test for presence of *Mycoplasma* infection. Other background assays did not generate any amplicon due to the presence of background organisms. These results are summarized in Table 4.

In order to test for sensitivity of detection of *Mycoplasma* templates, serial dilutions of genomic DNA of several *Mycoplasma* species were used as templates and the amplicons were analyzed. FIG. 5 shows such analyses for eight *Mycoplasma* species most commonly found in infected cell cultures. For all the *Mycoplasma* species detected we were able to detect at least 100 copies of *Mycoplasma* DNA.

Identification of Mycoplasma Infection by Restriction Digest Analyses

Since the 16S-23S intergenic region is not conserved among the Mollicutes, different enzymes were used for restriction analyses of the *Mycoplasma* amplicons generated by the assay described above. With a careful selection, one can use a few selected endonucleases to generate a restriction pattern specific for each of the *Mycoplasma* species. The endonucleases were selected based on the sequence data of the intergenic regions available in Gene bank. The presence of the restriction sites was confirmed by sequencing the generated amplicons as well as via endonuclease restriction analyses. FIG. 6 shows the results of restriction digest analyses for the eight most common types of *Mycoplasma* infections. The results for all the detected species are summarized in the Table 3.

Template Preparation

All the studies conducted above have used purified genomic DNA using methods commercially available for preparation of DNA. In order to insure a rapid preparation of the template without compromising the sensitivity of the assay, a lysis solution was developed where, during the incubation, the cells were lysed and treated with proteinase K for protein degradation. The proteinase K was then inactivated by heating the samples at 95° C. for 10 minutes as described in the Material and Methods section.

To test for the efficiency of the preparation methods, known concentrations of colony forming units of *Mycoplasma* were mixed with $10^5$ cells from two cell lines; a suspension cell line, K562, and LoVo, an adherent cell line. The mixture of *Mycoplasma* and eukaryotic cells was then lysed and the prepared template was tested for detection of *Mycoplasma* by PCR. FIG. 7 shows the result of the assay. As shown, at least 100 colony forming units were detected using the PCR assay described above. No amplicons were observed when eukaryotic cells were used as a template. These results show that using a cell lysate as a template does not compromise the sensitivity and the specificity of the detection. Detection of the *Mycoplasma* templates is as efficient as when purified genomic DNA is used as template.

Trial Testing of Infected Cell Cultures with Optimal Template Preparation, Primers, Internal Control and Optimized PCR Conditions.

The goal of this experiment was to verify the signal to noise ratio using the PCR-based assay described above under its optimized conditions. Additionally, the results obtained by PCR were compared with the results For this, six cell lines infected with *Mycoplasma* were obtained by two established methods for detection of *Mycoplasma*, Hoechst staining and direct culturing in liquid broth as well as solid agar. used as templates in the PCR-based assay. The same cell lines were tested for presence of *Mycoplasma* using the existing methods. The PCR analyses as shown in FIG. 8, produced unambiguous information. Moreover, restriction endonuclease analyses of the amplicon gave clearly identification of the *Mycoplasma* species present in each cell line. Table 5 shows a comparison of the results obtained by PCR and the other methods.

Discussion and Conclusions

The class Mollicutes includes five genera, *Mycoplasma, Acholeplasma, Ureaplasma, Phytoplasma* and *Spiroplasma*, which have significant medical, veterinary, and agricultural importance. The main purpose of this study was to evaluate a method utilizing the 16S-23S intergenic spacer of the rrn operon for a rapid and reliable identification of Mollicutes species known to be common cell line contaminants.

Currently, the number of biochemical reactions suitable for phenotypic characterization of Mollicutes is small, and therefore the current strategy of Mollicutes identification to the species level basically relies on serological features (Volokhov, D., V. Chizhikov, K. Chumakov, and A. Rasooly. 2003. Microarray-based identification of thermophilic *Campylobacter jejuni, C. coli, C. lari,* and *C. upsaliensis*. J Clin Microbiol 41:4071-80). The identification scheme is labor-intensive, time-consuming, and requires a complete serum panel to all known Mollicutes species. Due to the complexity of such assays, only a small number of laboratories are capable of carrying out all essential procedures for species identification.

The 16S rRNA gene, a common molecular marker of eubacteria, was shown to be a valuable complementary marker for species identification by using different molecular biological techniques such as denaturing gradient gel electrophoresis (Razin, S. 1994. DNA probes and PCR in diagnosis of mycoplasma infections. Mol Cell Probes 8:497-511), gene sequencing (Gray, L. D., K. L. Ketring, and Y. W. Tang. 2005. Clinical use of 16S rRNA gene sequencing to identify *Mycoplasma felis* and *M. gateae* associated with feline ulcerative keratitis. J Clin Microbiol 43:3431-4, Uphoff, C. C., and H. G. Drexler. 2004. Detection of *Mycoplasma* contaminations. Methods Mol Biol 290:13-24), restriction analysis (Wang, H., F. Kong, P. Jelfs, G. James, and G. L. Gilbert. 2004. Simultaneous detection and identification of common cell culture contaminant and pathogenic mollicutes strains by reverse line blot hybridization. Appl Environ Microbiol 70:1483-6), etc. However, recent analysis of 16S rRNA gene sequences of other species has shown the existence of several pairs of Mollicutes species which exhibit a high percent of homology. For example, *M. indiense* and *M. orale*, *M. cloacale* and *M. anseris, M. gallisepticum* and *M. imitans, M. cottewii* and *M. yeatsii* have 99.2%, 98.2%, 99.9%, and 99.7% nucleotide similarity between them, respectively (Volokhov, D., George, J., Liu, S., Ikonomi, P., Anderson, C., Chizhikov, V., 2006. Sequencing of the intergenic 16S-23S rRNA spacer (ITS) region of Mollicutes species and their identification using microarray-based assay and DNA sequencing. *Appl Microbiol Biotechnol.* 10:1-1), thus supporting previous observations that 16S rRNA gene sequence analysis is not a sufficient genetic marker by itself for identification of the species.

The universal PCR primers capable of amplifying the 16S-23S intergenic region were designed during this study. The results obtained by several groups demonstrated that the sequence variability in this region and the presence of conserved flanking regions make the 16S-23S intergenic region a valuable marker for species identification purposes. The relatively higher percentage of interspecies diversity of the intergenic region allows the application of a PCR-endonuclease restriction approach for identification of target species (Table 3). The key factor for efficiency of ITS sequences for species identification is intraspecies variability. As a general conclusion, ITS sequences appeared to a suitable marker for Mollicutes identification analyses due to their higher interspecies and low intraspecies variability.

As shown in the described experiments, the primer mix is designed to hybridize in the conserved region of 16S-23S intergenic region, and can detect at least 49 species of all Mollicutes including *Mycoplasma, Acholeplasma, Ureaplasma* and *Spiroplasma*.

One of our research goals was to assess the efficiency of our approach not only for detection of the Mollicutes species but also for their rapid speciation. The instant method, based on the variability of the 16S-23S intergenic region, relies on endonuclease restriction analyses selective of amplified sequences. The main advantage of this approach is to identify the origin of contamination by a fairly rapid and inexpensive method. The variability of the intergenic region makes possible the selection of a few endonucleases that would generate a distinct pattern of endonuclease digestion easily used for species identification. Although not a high throughput method, this method ensures speciation analyses of amplified amplicons within a short time. Moreover, using this approach, it is possible to confirm the presence of multiple infections within the cell culture.

Development of new methods that rely on the use of sequence variation is highly advantageous and valuable for rapid monitoring and screening of potential *Mycoplasma* contamination of cell cultures used for production of biological products. The combination of specific PCR and speciation analysis of the resulting amplicons can open a real opportunity not only to detect the presence of *Mycoplasma* DNA in samples, but also to perform contaminant characterization. For high throughput analyses, a combination of PCR and hybridization assay, such as microarrays could be imagined. However, the application of a microarray-based technology as a routine testing in research laboratories is very unlikely since the cost of such analyses remains considerable. Therefore, the restriction digest analyses of the amplified *Mycoplasma* products is a simplified and affordable speciation test.

Development of rapid methods for detecting *Mycoplasma* will facilitate and expedite regulatory evaluation and licensure of vaccines and other products produced in cell culture. Progress in the development of new biological products with short shelf lives has also demonstrated the urgent need for development of new tests that can be completed in a short time and guarantee the safety of those products (chondrocyte allograft, autologous chondrocyte implantation, activated lymphocytes transfusion, and stem cell implantation).

We have successfully used this approach in earlier studies for the detection and discrimination of different viral and bacterial pathogens from closely related nonpathogenic species (Jules Mattes, M. 2004. Control of the mycoplasma epidemic. In Vitro Cell Dev Biol Anim 40:253-4.; Hopert A, Uphoff C C, Wirth H. Hauser H. Drexler H O. (1993) Specificity and sensitivity of polymerase chain reaction in comparison with other methods for the detection of *Mycoplasma* contamination in i cell lines. J Immunol Methods. 164: 91-100; Kong F. James G. Gordon S. Zelyski A, Gilbert G L. (2001) Species Specific PCR for Identification of Common Contaminant Mollicutes in Cell Culture. Appl Environ Microbiol. 67: 3195-200; Dorigo-zetsma J. W., Zaat S A J, Wertheim-van D, Spanjeard P M E, Rijntjes J. Waveren V, Jensen J S, Angulo A F, Dankert J. (1997) Comparison of PCR, culture, and serological tests for diagnosis of *Mycoplasma* pneumonias respiratory tract infection in children. J Clin! to Microbiol. 37: 14-7; Jensen J S, Borre M B, Dohn B. (2003) Detection of *Mycoplasma genifalium* by PCR Amplification of the 16S rRNA Gene. J Clin Microbiol. 41: 261-266.). The simplicity of the proposed microarray protocol for simultaneous identification of numerous Mollicutes species and the ability to perform accurate analysis of multiple samples in a relatively short period compared to currently routinely used protocols present a great improvement for a Mollicutes identification scheme.

TABLE 1

List of *Mollicutes* tested by PCR and size of the amplicons generated for each template. Copy number for genomic DNA is listed.

| | ATCC Catalog Nr. | Size of Amplicon | Sensitivity (copy nr.) |
|---|---|---|---|
| 8 Common Species | | | |
| 1. *A. laidlawii* | 23206 | 936, 682 | 100 |
| 2. *M. arginini* | 23243& 23838D | 423 | 100 |
| 3. *M. fermentans* | 19989D | 547 | 100 |
| 4. *M. hominis* | 23114 | 425 | 100 |
| 5. *M. hyorhinis* | 23234& 17981D | 504 | 100 |
| 6. *M. orale* | 23714D | 479 | 100 |
| 7. *M. pirum* | 25960D | 515 | 100 |
| 8. *M. salivarium* | 23577& 14277 | 445 | 100 |
| 29 Additional Species | | | |
| 9. *A. granularum* | 19168 | 876 | n/a |
| 10. *A. oculi* | 27350 | 682 | 100 |
| 11. *M. anatis* | 25524 | 512 | 100 |

TABLE 1-continued

List of *Mollicutes* tested by PCR and size of the amplicons generated for each template. Copy number for genomic DNA is listed.

| | ATCC Catalog Nr. | Size of Amplicon | Sensitivity (copy nr.) |
|---|---|---|---|
| 12. *M. arthritidis* | 19611D | 463 | 100 |
| 13. *M. bovigenitalium* | 19852 | 541 | 200 |
| 14. *M. bovirhinis* | 27748 | 534 | 100 |
| 15. *M. bovis* | 25523 | 544 | 100 |
| 16. *M. buccale* | 23636 | 464 | 100 |
| 17. *M. californicum* | 33461 | 544 | 100 |
| 18. *M. canadense* | 29418 | 423 | 100 |
| 19. *M. caviae* | 27108 | 536 | 200 |
| 20. *M. columbinasale* | 33549 | 578 | 100 |
| 21. *M. columbinim* | 29257 | 567 | 200 |
| 22. *M. columorale* | 29258 | 527 | 100 |
| 23. *M. cricetuli* | 35279 | 513 | 10,000 |
| 24. *M. equirhinis* | 29420 | 422 | 100 |
| 25. *M. faucium* | 25293 | 456 | 100 |
| 26. *M. gallinaceum* | 33550 | 529 | 100 |
| 27. *M. gallisepticum* | 15302 | 794 | 10,000 |
| 28. *M. gateae* | 23392 | 420 | 100 |
| 29. *M. glycophilium* | 35277 | 542 | 100 |
| 30. *M. hyopneumoniae* | 25934 | 738 | 100 |
| 31. *M. hyosynoviae* | 25591 | 445 | 100 |
| 32. *M. lipophilum* | 27104 | 533 | 1,000 |
| 33. *M. neurolyticum* | 19988 | 558 | 10,000 |
| 34. *M. penetrans* | 55252 | 487 | 1,000 |
| 35. *M. pulmonis* | 19612 | 534 | 10,000 |
| 36. *S. apis* | 33834 | 550 | 10,000 |
| 37. *S. citri* | 27556 | 517 | 10,000 |
| Other Species | | | |
| 38. *M. capricolum* | 27343 | 450 | n/a |
| 39. *M. cloacale* | 35276 | 437 | 1,000 |
| 40. *M. falconis* | 51372 | 434 | 100 |
| 41. *M. genitalium* | 33530D | 445 | 10,000 |
| 42. *M. maculosum* | 19327 | 548 | 100 |
| 43. *M. opalescens* | 27921 | 543 | 1,000 |
| 44. *M. pneumoniae* | 15531 | 470 | 1,000 |
| 45. *M. primatum* | 25948 | 549 | 200 |
| 46. *M. spermatophilum* | 49695 | 552 | 1,000 |
| 47. *M. synoviae* | 25204 | No bands detected | |
| 48. *U. urealyticum* | 27618 | 539 | 100 |
| 49. *M. bovoculi* | 29104 | 473 | 100 |
| 50. *M. mobile* | 43663 | 548 | 1,000 |
| 51. *S. floricola* | 29989 | 541 | 100 |
| | | | n/a |
| | | | 1,000 |
| | | | 100 |
| | | | 10,000 |
| | | | 100 |
| | | | 1,000 |
| | | | n/a |
| | | | 1,000 |
| | | | 100 |
| | | | 10,000 |
| | | | 100 |
| | | | 1,000 |
| | | | n/a |
| | | | 1,000 |
| | | | 100 |
| | | | 10,000 |
| | | | 100 |
| | | | 1,000 |
| | | | 1,000 |

TABLE 2

List of cell lines used for detection of *Mycoplasma* infection and assay optimization.

| Name | Source | Mycoplasma Infection | Growth Conditions |
|---|---|---|---|
| TL-4000 | ATCC (cat #) | *A. laidlawii* | MEM + 10% FBS |
| K562-4 | ATCC (cat #) | *M. arginini* | IMDM + 10% FBS |
| HB-17 | ATCC (cat #) | *M. fermentans* | IMDM + 10% FBS |
| TL-1276 | ATCC (cat #) | *M. hyorhinis* | Ham's F12K + 10% FBS |
| CRL-2891 | ATCC (cat #) | *M. orale* | MEM + 10% FBS |
| CRL-2897 | ATCC (cat #) | *M. salivarium* | MEM + 10% FBS |
| K562 | ATCC (cat #) | None | IMDM + 10% FBS |
| LoVo | ATCC (cat #) | None | Ham's F12K + 10% FBS |

TABLE 3

Size of PCR products and their restriction digestion fragments for various *Mollicutes*

| Species | Size of PCR Product (bp) | AseI | Rsa I | Sau3A | SspI |
|---|---|---|---|---|---|
| Most Common | | | | | |
| *A. laidlawii* | 936, 682 | 682, 609, 237, 90 | 689, 481, 222, 201, 25 | 582, 468, 306, 100, 98, 48, 18 | 936, 513, 169 |
| *M. arginini* | 423 | 285, 138 | 243, 157, 23 | 161, 142, 120 | 287, 136 |
| *M. fermentans* | 547 | 412, 135 | 354, 148, 23, 12, 10 | 394, 153 | 294, 253 |
| *M. hominis* | 425 | 270, 151, 4 | 245, 156, 24 | 142, 134, 133, 16 | 203, 119, 75, 28 |
| *M. hyorhinis* | 504 | None | 325, 156, 23 | 311, 193 | 369, 91, 44 |
| *M. orale* | 479 | 301, 178 | 300, 156, 23 | 320, 159 | 223, 147, 74, 29, 6 |
| *M. pirum* | 515 | 320, 195 | 378, 114, 23 | 355, 145, 15 | 303, 212 |
| *M. salivarium* | 445 | None | 273, 156, 16 | 172, 150, 123 | 221, 107, 88, 29 |
| Less Common | | | | | |
| *A. granularum* | 876 | 637, 239 | 454, 221, 201 | 440, 289, 100, 47 | no |
| *A. oculi* | 682 | None | 434, 201, 47 | 286, 246, 104, 46 | None |
| *M. anatis* | 512 | None | 240, 157, 74, 22, 10, 9 | 287, 225 | 218, 215, 79 |

TABLE 3-continued

Size of PCR products and their restriction digestion fragments for various *Mollicutes*

| Species | Size of PCR Product (bp) | AseI | Rsa I | Sau3A | SspI |
|---|---|---|---|---|---|
| *M. arthritidis* | 463 | 306, 157 | 284, 156, 23 | 166, 157, 140 | 310, 153 |
| *M. bovigenitalium* | 541 | 391, 150 | 370, 148, 23 | None | 314, 217, 10 |
| *M. bovirhinis* | 534 | 337, 197 | 353, 157, 24 | None | 455, 79 |
| *M. bovis* | 544 | 215, 177, 112, 40 | 372, 148, 24 | 528, 16 | 331, 213 |
| *M. buccale* | 464 | 310, 154 | 285, 156, 23 | 168, 161, 135 | 230, 123, 82, 29 |
| *M. californicum* | 544 | None | 373, 95, 52, 24 | None | 316, 218, 10 |
| *M. canadense* | 423 | 280, 143 | 243, 156, 24 | 158, 139, 126 | 284, 139 |
| *M. caviae* | 536 | None | 365, 148, 23 | 383, 153 | 283, 253 |
| *M. columbinasale* | 578 | 378, 173, 27 | 407, 148, 23 | 429, 134, 15 | 382, 196 |
| *M. columbinum* | 567 | None | 395, 148, 24 | 417, 150 | 358, 209 |
| *M. columorale* | 527 | 197, 197, 133 | 282, 157, 64, 24 | 368, 159 | None |
| *M. cricetuli* | 513 | 222, 122, 76, 59, 34 | 332, 157, 24 | None | None |
| *M. equirhinis* | 422 | 272, 142, 8 | 242, 156, 24 | 158, 125, 75, 64 | 202, 138, 82 |
| *M. faucium* | 456 | 305, 151 | 276, 156, 24 | 164, 158, 134 | 309, 118, 29 |
| *M. gallinaceum* | 529 | 324, 205 | 349, 157, 23 | None | 226, 212, 91 |
| *M. gallisepticum* | 794 | 609, 185 | 658, 113, 23 | 417, 348, 29 | 732, 62 |
| *M. gateae* | 420 | 277, 143 | 240, 156, 24 | 158, 136, 126 | 281, 139 |
| *M. glycophilium* | 542 | 349, 193 | 294, 157, 68, 23 | None | None |
| *M. hyopneumoniae* | 738 | 376, 362 | 715, 23 | 520, 218 | 512, 226 |
| *M. hyosynoviae* | 445 | 303, 142 | 206, 156, 60, 23 | 163, 157, 125 | 307, 109, 29 |
| *M. lipophilum* | 533 | None | 289, 146, 75, 23 | 287, 147, 64, 35 | None |
| *M. neurolyticum* | 558 | 302, 256 | 378, 156, 24 | 400, 158 | 346, 190, 22 |
| *M. penetrans* | 487 | None | 267, 112, 85, 23 | 329, 158 | 203, 147, 137 |
| *M. pulmonis* | 534 | 331, 203 | 353, 157, 24 | 206, 169, 159 | None |
| *S. apis* | 550 | None | None | 267, 166, 105, 12 | None |
| *S. citri* | 517 | None | 375, 119, 23 | 358, 159 | None |
| Other Species | | | | | |
| *M. cloacale* | 437 | 283, 154 | 257, 156, 24 | 158, 143, 136 | 287, 120, 30 |
| *M. falconis* | 434 | 275, 155, 4 | 211, 156, 44, 23 | 157, 139, 138 | 201, 151, 82 |
| *M. genitalium* | 445 | 231, 214 | 307, 115, 23 | 204, 161, 80 | 388, 57 |
| *M. maculosum* | 548 | 193, 180, 175 | 376, 148, 24 | None | None |
| *M. opalescens* | 543 | 347, 196 | 371, 148, 24 | 393, 150 | 326, 217 |
| *M. pneumoniae* | 470 | None | 336, 113, 21 | 232, 157, 81 | 415, 55 |
| *M. primatum* | 549 | 413, 136 | 377, 148, 24 | None | 330, 219 |
| *M. spermatophilum* | 552 | None | 381, 148, 23 | 403, 149 | None |
| *U. urealyticum* | 539 | 420, 115, 4 | 328, 175, 24, 12 | 196, 179, 105, 55, 4 | 237, 218, 61, 23 |
| *M. bovoculi* | 473 | None | 449, 24 | 255, 218 | None |
| *M. mobile* | 548 | None | None | 153, 142, 132, 79, 27, 15 | 215, 213, 108, 12 |
| *S. floricola* | 541 | 404, 111, 26 | 399, 71, 48, 23 | 378, 163 | 327, 214 |

TABLE 4

Performance of the PCR assay in the presence of background cells. Several cell lines were used for this assay as well as several species of prokaryotes; fungi and yeast that are more often found in cell culture contaminants.

| Species | Source | Nr of cells per PCR assay | Background Noise | Detection of Internal Control |
|---|---|---|---|---|
| *Drosophila* | Invitrogen (11496-015) | $10-10^6$ | − | + |
| Mouse | ATCC (CRL-2036, TIB-158) | $1000-10^6$ | − | + |
| Human | ATCC (CCL-119, CCL-114) | $1000-10^6$ | − | + |
| Monkey | ATCC (CCL-26, CRL-1805, CRL-1688, CRL-1576) | $1000-10^6$ | − | + |
| Hamster | ATCC (CRL-1859, CCL-61) | $1000-10^6$ | − | + |
| Rat | ATCC (CCL-216, CRL-1607) | $1000-10^6$ | − | + |
| *B. subtilis* | ATCC (6051) | $1-5 \times 10^6$ | − | + |
| *E. faecalis* | ATCC (19433) | $1-5 \times 10^6$ | − | + |
| *C. albicans* | ATCC 10231 | $1-6 \times 10^6$ | − | + |

TABLE 4-continued

Performance of the PCR assay in the presence of background cells. Several cell lines were used for this assay as well as several species of prokaryotes; fungi and yeast that are more often found in cell culture contaminants.

| Species | Source | Nr of cells per PCR assay | Background Noise | Detection of Internal Control |
|---|---|---|---|---|
| A. versicolor | ATCC (11730) | $1\text{-}2 \times 10^6$ | – | + |
| C. cladosporiodes | ATCC (38810) | $1\text{-}1.7 \times 10^6$ | – | + |
| E. coli | ATCC (11775) | $1\text{-}5 \times 10^6$ | Amplification over $5 \times 10^4$ cells | + |

TABLE 5

Detection of Mycoplasma infection in various infected cell lines. Comparison of the PCR-based approach with existing detection methods.

| | Mycoplasma Detection Assays | | |
|---|---|---|---|
| Cell Lines | PCR | Hoechst Staining | Direct Culture |
| HB-17/M. fermentans | + | + | + |
| K562/M. arginini | + | + | + |
| TL1276/M. hyorhinis | + | + | + |
| Tl-4000/A. laidlawii | + | + | + |
| CRL-2891/M. orale | + | + | + |
| BHK/M. salivarium | + | + | + |
| BHK/M. hominis | + | + | + |
| CRL-2421/M. prirum | + | + | + |

It is evident from examples that the present methods can be more sensitive than methods that are currently publicly available, and that they can reduce the time necessary to identify Mycoplasma infection of a sample by reducing the number of cycles necessary to detect the bacteria.

All patents, patent applications, and published references cited herein are hereby incorporated by reference in their entirety. While this invention has been particularly shown and described with references to various embodiments, it is to be understood that various changes can be made without departing from the scope of the invention.

EQUIVALENTS

Those skilled in the art will recognize, or be able to ascertain using no more than routine experimentation, many equivalents to the specific embodiments of the invention described herein. Such equivalents are intended to be encompassed by the following claims.

The invention claimed is:

1. An oligonucleotide primer consisting of SEQ ID NO:1, SEQ ID NO:2, SEQ ID NO:3, SEQ ID NO:4, SEQ ID NO:5, SEQ ID NO:6, SEQ ID NO:7, SEQ ID NO:8, or SEQ ID NO:9.

2. A composition comprising at least one oligonucleotide primer, each of said at least one primer consisting of SEQ ID NO:1, SEQ ID NO:2, SEQ ID NO:3, SEQ ID NO:4, SEQ ID NO:5, SEQ ID NO:6, SEQ ID NO:7, SEQ ID NO:8, or SEQ ID NO:9.

3. A composition comprising a primer a sequence consisting of SEQ ID NO:1 and a primer sequence consisting of SEQ ID NO:2.

4. The composition of claim 3, further comprising a primer consisting of SEQ ID No: 3 and a primer consisting of SEQ ID NO: 4.

5. The composition of claim 3, further comprising an amplification control nucleic acid and at least one oligonucleotide primer specific for said amplification control nucleic acid.

6. The composition of claim 3, further comprising Taq polymerase.

7. The composition of claim 3, further comprising a dye that can specifically detect double stranded DNA.

8. A kit comprising the composition of claim 3 in a first container.

9. The kit of claim 8, further comprising genomic or subgenomic *Mycoplasma* or *Acholeplasma* nucleic acids in a second container.

10. The kit of claim 8, further comprising an amplification control nucleic acid, wherein said amplification control nucleic acid is present in said first container or in a second container.

11. The kit of claim 8, further comprising reagents and supplies for purification of nucleic acids.

12. The kit of claim 8, further comprising, in packaged combination, SYBR® Green dye, an amplification control, a *Mycoplasma* control, an *Acholeplasma* control, a reference dye, a template dependent nucleic acid extending enzyme, and all reagents and supplies necessary to purify nucleic acids.

* * * * *